(12) United States Patent
Sandstedt et al.

(10) Patent No.: US 7,281,795 B2
(45) Date of Patent: Oct. 16, 2007

(54) LIGHT ADJUSTABLE MULTIFOCAL LENSES

(75) Inventors: Christian A. Sandstedt, Pasadena, CA (US); Jagdish M. Jethmalani, San Diego, CA (US); Shiao H. Chang, Pasadena, CA (US)

(73) Assignee: Calhoun Vision, Inc., Pasadena, CA (US)

( * ) Notice: Subject to any disclaimer, the term of this patent is extended or adjusted under 35 U.S.C. 154(b) by 236 days.

(21) Appl. No.: 11/083,794

(22) Filed: Mar. 18, 2005

(65) Prior Publication Data

US 2005/0187622 A1 Aug. 25, 2005

Related U.S. Application Data

(63) Continuation-in-part of application No. 10/915,948, filed on Aug. 11, 2004, now abandoned, and a continuation-in-part of application No. 10/328,859, filed on Dec. 24, 2002, now abandoned, and a continuation-in-part of application No. 10/175,552, filed on Jun. 18, 2002, now Pat. No. 7,210,783, which is a continuation of application No. 09/416,044, filed on Oct. 8, 1999, now Pat. No. 6,450,642.

(60) Provisional application No. 60/494,969, filed on Aug. 13, 2003, provisional application No. 60/115,617, filed on Jan. 12, 1999, provisional application No. 60/132,871, filed on May 5, 1999, provisional application No. 60/140,298, filed on Jun. 17, 1999.

(51) Int. Cl.
*G02C 7/04* (2006.01)
*A61F 2/16* (2006.01)

(52) U.S. Cl. ................ 351/161; 351/177; 623/6.24

(58) Field of Classification Search .............. 351/161, 351/168, 177; 623/6.24
See application file for complete search history.

(56) References Cited

U.S. PATENT DOCUMENTS

| 4,787,903 | A | 11/1988 | Grendahl |
| 5,997,140 | A | 12/1999 | Zhang et al. |
| 6,450,642 | B1 * | 9/2002 | Jethmalani et al. ......... 351/219 |
| 2002/0016629 | A1 | 2/2002 | Sandstedt et al. |
| 2002/0100990 | A1 | 8/2002 | Platt et al. |
| 2005/0036106 | A1 | 2/2005 | Dreher |

FOREIGN PATENT DOCUMENTS

| FR | 2 657 294 | 7/1991 |
| WO | WO-1998/05272 | 2/1998 |
| WO | WO-2001/71411 | 9/2001 |
| WO | WO 03/058296 | 7/2003 |
| WO | WO 2005016191 | 2/2005 |

OTHER PUBLICATIONS

International Preliminary Report on Patentability & the Written Opinion of the International Searching Authority issued for PCT/US2004/026386 dated Feb. 13, 2006.
Partial European Search Report for application EP 06 25 1320 dated Jun. 23, 2006.
Supplementary Partial European Search Report issued for EP 02 80 6216, dated Mar. 29, 2007.

* cited by examiner

*Primary Examiner*—Scott J. Sugarman
(74) *Attorney, Agent, or Firm*—Fulbright & Jaworski LLP

(57) ABSTRACT

The invention relates to novel intraocular lenses. The lenses are capable of post-operative adjustment of their optical properties, including conversion from single focal lenses to multifocal lenses.

8 Claims, 12 Drawing Sheets

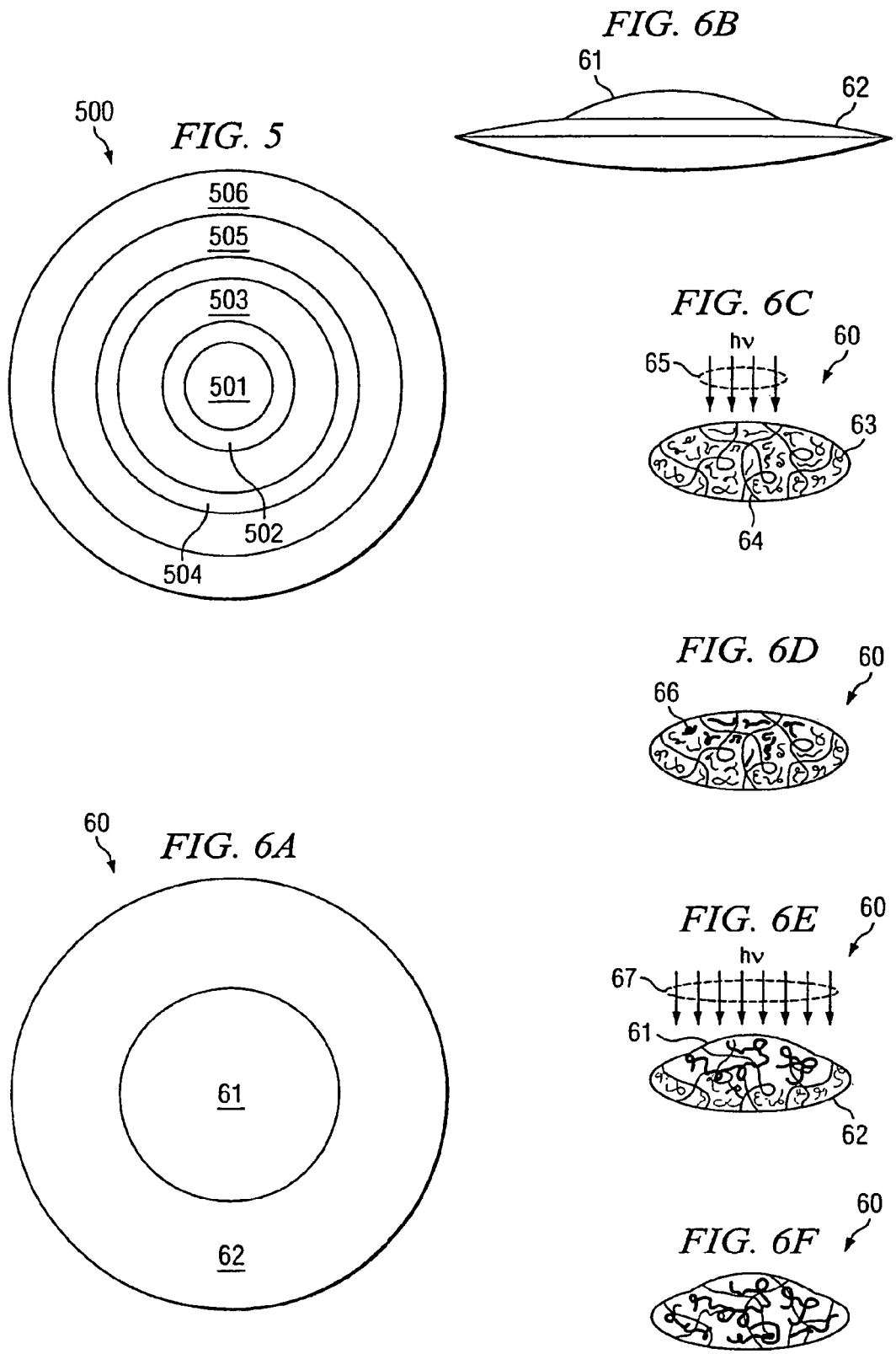

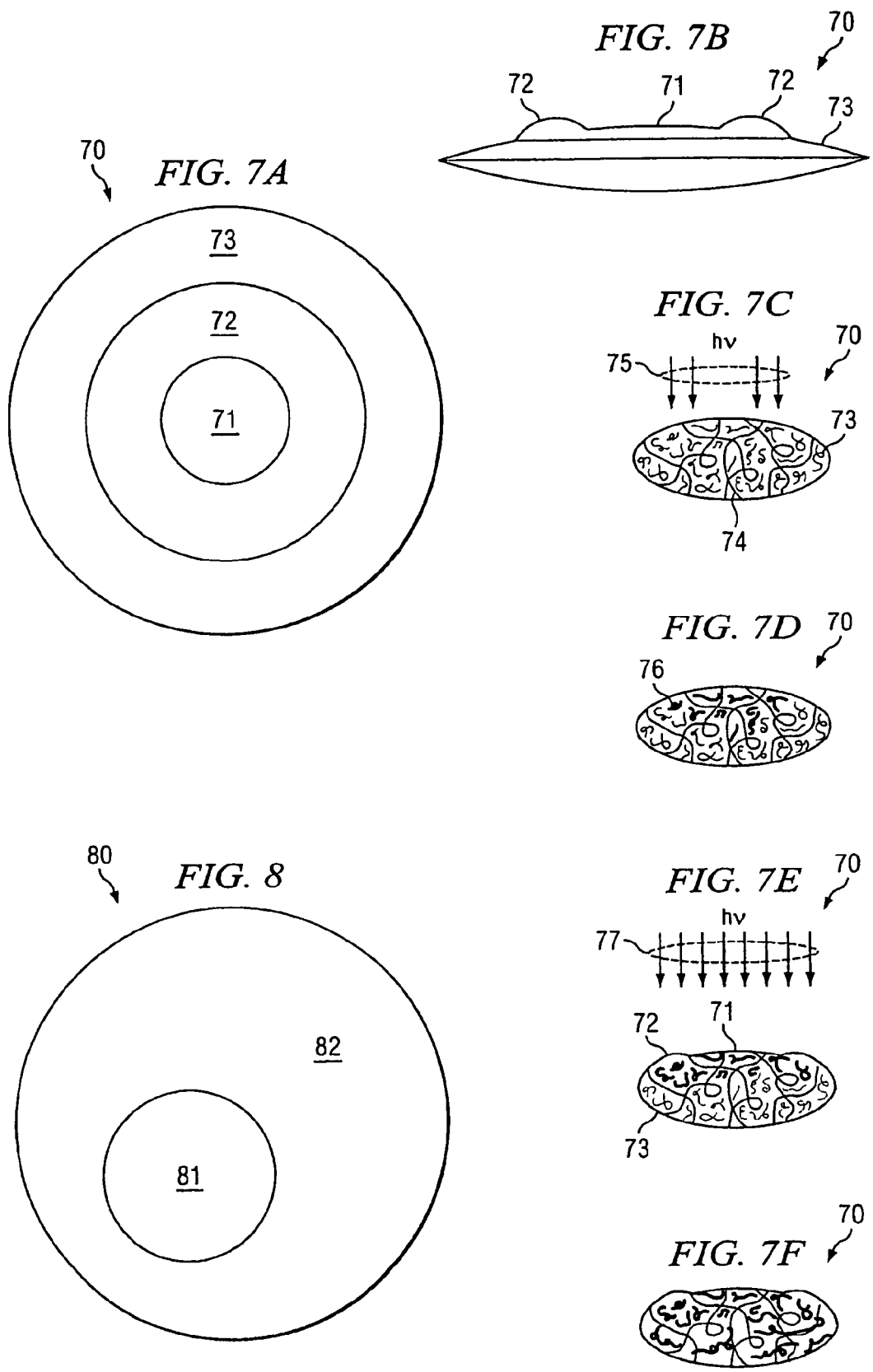

LIGHT ADJUSTABLE MULTIFOCAL LENSES

CROSS-REFERENCE TO RELATED APPLICATIONS

This application claims priority benefit of U.S. Provisional Patent Application No. 60/494,969 entitled "LIGHT ADJUSTABLE MULTIFOCAL LENSES," filed Aug. 13, 2003, and is a continuation-in-part of U.S. patent application Ser. No. 10/915,948 entitled "LIGHT ADJUSTABLE MULTIFOCAL LENSES," filed Aug. 11, 2004, now abandoned the disclosures of which are hereby incorporated herein by reference and is a continuation-in-part of U.S. patent application Ser. No. 10/328,859 entitled "LIGHT ADJUSTABLE MULTIFOCAL LENSES," filed Dec. 24, 2002, now abandoned and this application is a continuation in part of U.S. application Ser. No. 10/175,552 filed Jun. 18, 2002, now U.S. Pat. No. 7,210,783 which is a continuation of U.S. application Ser. No. 09/416,044, filed Oct. 8, 1999, now U.S. Pat. No. 6,450,642 which issued on Sep. 17, 2002 and claims the benefit of (i) U.S. Provisional Application No. 60/115,617 filed Jan. 12, 1999 filed by inventors Jagdish M. Jethmalani, Daniel M. Schwartz, Julie A. Komfield, and Robert H. Grubbs entitled SILICONE IOLS EMBEDDED WITH PHOTOSENSITIVE COMPOSITIONS; (ii) U.S. Provisional Application No. 60/132,871 filed May 5, 1999 filed by inventors Jagdish M. Jethmalani, Daniel M. Schwartz, Julie A. Komfield, Robert H. Grubbs, and Christian A. Sandstedt entitled SILICONE IOLS EMBEDDED WITH PHOTO-SENSITIVE COMPOSITIONS; and (iii) U.S. Provisional Application No. 60/140,298 filed Jun. 17, 1999 filed by inventors Jagdish M. Jethmalani, Daniel M. Schwartz, Julie A. Komfield, Robert H. Grubbs, and Christian A. Sandstedt entitled SILICONE IOLS EMBEDDED WITH PHOTOSENSITIVE COMPOSITIONS, all three of which are incorporated herein by reference in their entireties.

TECHNICAL FIELD

The invention relates to optical elements, which can be modified post-manufacture such that different versions of the element will have different optical properties. In one embodiment, it relates to lenses, such as intraocular lenses, which can be converted into multifocal lenses post-fabrication.

BACKGROUND OF THE INVENTION

Accommodation, as it relates to the human visual system, refers to the ability of a person to use their unassisted ocular structure to view objects at both near (e.g. reading) and far (e.g. driving) distances. The mechanism whereby humans accommodate is by contraction and relaxation of the cilliary body which inserts into the capsular bag surrounding the natural lens. Under the application of cilliary stress, the human lens will undergo a shape change effectively altering the radius of curvature of the lens. This action produces a concomitant change in the power of the lens. However, as people grow older the ability for them to accommodate reduces dramatically. This condition is known as presbyopia and currently affects more than 90 million people in the US. The most widely believed theory to explain the loss of accommodation was put forth by Helmholtz and states that as the patient ages, the crystalline lens of the human eye becomes progressively stiffer prohibiting deformation under the applied action of the cilliary body.

People who can see objects at a distance without the need for spectacle correction, but have lost the ability to see objects up close are usually prescribed a pair of reading glasses or magnifiers. For those patients who have required previous spectacle correction due to preexisting defocus andor astigmatism the patient is prescribed a pair of bifocals, trifocals, variable, or progressive focus lenses that allow the person to have both near and distance vision. Compounding this condition is the risk of cataract development as the patient ages. In fact, cataract extraction followed by intraocular lens (IOL) implantation is the most commonly performed surgery in patients over 65 years old (reference).

To effectively treat both presbyopia and cataracts the patient can be implanted with a multifocal IOL. The general concepts and designs of multifocal IOLs have been described before in the ophthalmic and patent literature. The simplest design for a multifocal IOL is commonly referred to as the "bull's eye" configuration and comprises a small, central add zone (1.5 mm to 2.5 mm in diameter) that provides near vision ("Intraocular Lenses in Cataract and Refractive Surgery," D. T. Azar, et. al., W. B. Saunders Company (2001); "Intraocular Lenses: Basics and Clinical Applications," R. L. Stamper, A Sugar, and D. J. Ripkin, American Academy of Ophthalmology (1993), both of which are hereby incorporated herein by reference). The power of the central add zone is typically between 3 to 4 diopters greater than the base power of the IOL, which translates to an effective add of 2.5 to 3.5 diopters for the entire ocular system. The portion of the lens outside the central add zone is referred to as the base power and is used for distance viewing. In theory, as the pupil constricts for near viewing, only that central add zone of the lens will have light from the image passing through it. However, under bright viewing conditions the pupil will also constrict leaving the patient 2 to 3 diopters myopic. This can be potentially problematic for a person who is driving in a direction with the sun shining straight at them, e.g. driving west around the time of sunset. To counteract this problem, an annular design with the central and peripheral portion of the lens designed for distance viewing and a paracentral ring (2.1 to 3.5 mm) for near vision. This design will maintain distance viewing even if the pupil constricts (*Intraocular Lenses in Cataract and Refractive Surgery*, D. T. Azar, et. al., W. B. Saunders Company (2001); "Intraocular Lenses: Basics and Clinical Applications," R. L. Stamper, A Sugar, and D. J. Ripkin, American Academy of Ophthalmology (1993), which is hereby incorporated herein by reference). The most widely adopted multifocal IOL currently sold in the US is described in U.S. Pat. No. 5,225,858, which is hereby incorporated herein by reference. This IOL is known as the Array lens and comprises five concentric, aspheric annular zones. Each zone is a multifocal element and thus pupil size should play little or no role in determining final image quality.

However, as with standard intraocular lenses the power and focal zones of the lenses must be estimated prior to implantation. Errors in estimating the needed power as well as shifting of the lens post-operatively due to wound healing often results in less than optimal vision. The latter effect is particularly problematic for the case of the bull's eye lens if a transverse (perpendicular to the visual axis) shift of the IOL occurred during healing. This would effectively move the add part off the visual axis of the eye resulting in the lost of desired multifocality. The Array and paracentral IOL designs can partly overcome the dislocation problem during wound healing-although any IOL movement longitudinally (the direction along the visual axis), preexisting astigmatism, or astigmatism induced by the surgical procedure can not be compensated using these multifocal IOL designs. This results in the patient having to choose between additional surgery to replace or reposition the lens or to use additional corrective lenses.

A need exists for an intraocular lens which can be adjusted post-operatively in vivo to form a multifocal intraocular lens. This type of lens can be designed in-vivo to correct to an initial emmetropic (light from infinity forming a perfect focus on the retina) state and then the multifocality may be added during a second treatment. Such a lens would remove some of the guess work involved in presurgical power selection, overcome the wound healing response inherent to IOL implantation, allow the size of the add or subtract zone(s) to be customized to correspond to the patient's magnitude and characteristics of dilation under different illumination conditions, and allow the corrected zones to be placed along the patient's visual axis.

BRIEF SUMMARY OF THE INVENTION

Novel optical elements are provided whose properties can be adjusted post-manufacture to produce an optical element having different properties. Specifically, the invention relates to an intraocular lens that can be transformed into a multifocal lens after the lens has been implanted in the eye. In this manner, the intraocular and/or focal zones of the lens can be more precisely adjusted after the lens has been subjected to any post-operative migration, and can be based on input from the patient and standard refraction techniques rather than preoperative estimation.

The alteration of the optical element is accomplished through the use of a modifying composition ("MC") dispersed throughout the element. The MC is capable of polymerization when exposed to an external stimulus such as heat or light. The stimulus can be directed to one or more regions of the element causing polymerization of the MC only in the exposed regions. The polymerization of the MC causes changes in the optical properties of the element with exposed regions.

The inventive optical elements comprise a first polymer matrix and a refraction modulating composition dispersed therein. The first polymer matrix forms the optical element framework and is generally responsible for many of its material properties. The modifying composition ("MC") may be a single compound or a combination of compounds that is capable of stimulus-induced polymerization, preferably photo-polymerization. As used herein, the term "polymerization" refers to a reaction wherein at least one of the components of the refraction modulating composition reacts to form at least one covalent or physical bond with either a like component or with a different component. The identities of the first polymer matrix and the refraction modulating compositions will depend on the end use of the optical element. However, as a general rule, the first polymer matrix and the refraction modulating composition are selected such that the components that comprise the refraction modulating composition are capable of diffusion within the first polymer matrix. Put another way, a loose first polymer matrix will tend to be paired with larger MC components and a tight first polymer matrix will tend to be paired with smaller MC components.

Upon polymerization, several changes occur within the optical element. The first change is the formation of a second polymer network comprising polymerized MC. The formation of this polymer network can cause changes in the optical properties of the element, namely the refractive index. In addition, when the MC polymerizes, a difference in the chemical potential between the polymerized and unpolymerized region is induced. This in turn causes the unpolymerized MC to diffuse within the element, thermodynamic equilibrium of the optical element is reestablished. If the optical element possesses sufficient elasticity, this migration of MC can cause swelling of the element in the area exposed to the stimulus. This, in turn, changes the shape of the element, causing changes in the optical properties. Depending upon the nature of the optical element, the MC incorporated into the element, the duration, and the spatial intensity profile of the stimulus either or both of these two changes can occur.

One key aspect of the present invention is that the optical elements are self-contained in that once fabricated, no material is either added or removed from the lens to obtain the desired optical properties.

It has been found that by exposing different regions of the optical element to varying degrees or in a predetermined pattern of external stimulus, it is possible to vary the optical properties of the element in different regions. For example, it is possible through the use of various patterns, to create a central zone with one set of optical properties, surrounded by concentric rings of differing optical properties. In this way, a multifocal lens can be created. In another embodiment, customized bifocal, multifocal, etc. patterns can be written on the lens in one treatment followed by a second treatment to lock-in the unreacted modifying composition present throughout the entire lens. Alternately, multiple treatments of customized patterns can be written on the lens to provide patients with vision without the need for spectacles.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 5 is an example of a lens made according to embodiments of the invention.

FIGS. 6A through 6F depict a top-down view and a side view of an example of a multifocal lens according to embodiments of the invention.

FIGS. 7A through 7F depict a top-down view and a side view of an example of a multifocal lens according to embodiments of the invention.

FIG. 8 depicts a top-down view of an example of a multifocal lens according to embodiments of the invention.

DETAILED DESCRIPTION OF THE INVENTION

Figure 1A:
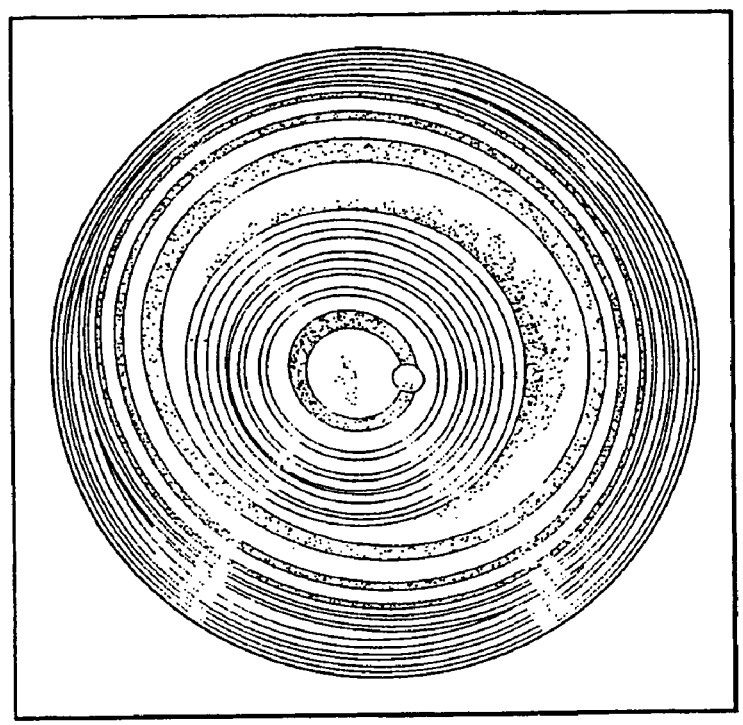
FIGS. 1A and 1B depict a cross-section of an intraocular lens and a micrograph, according to an embodiment of the invention.

The optical elements of the present invention are capable of post-fabrication alteration of optical properties. The elements are self-contained and do not require the addition or removal of materials to change the optical properties. Instead, the optical properties are altered by exposing a portion or portions of the optical element to an external stimulus which induces polymerization of a MC within the element. The polymerization of the MC, in turn, causes the change in optical properties.

The optical element of the invention has dispersed within it a MC. This MC is capable of diffusion within the element; can be readily polymerized by exposure to a suitable external stimulus; and is compatible with the materials used to make the optical element.

The optical element is typically made of a first polymer matrix. Illustrative examples of a suitable first polymer matrix include: polyacrylates such as polyalkyl acrylates and polyhydroxyalkyl acrylates; polymethacrylates such as polymethyl methacrylate ("PMMA"), polyhydroxyethyl methacrylate ("PHEMA"), and polyhydroxypropyl methacrylate ("HPMA"); polyvinyls such as polystyrene and polyvinylpyrrolidone ("PNVP"); polysiloxanes such as polydimethylsiloxane; polyphosphazenes, and copolymers of thereof. U.S. Pat. No. 4,260,725 and patents and references cited therein (which are all incorporated herein by reference) provide more specific examples of suitable polymers that may be used to form the first polymer matrix.

In preferred embodiments, where flexibility is desired, the first polymer matrix generally possesses a relatively low glass transition temperature ("$T_g$") such that the resulting IOL tends to exhibit fluid-like and or elastomeric behavior, and is typically formed by cross-linking one or more polymeric starting materials wherein each polymeric starting material includes at least one cross-linkable group. In the case of an intraocular lens, the $T_g$ should be less than 25° C. This allows the lens to be folded, facilitating implantation. In cases where rigidity is desired, the $T_g$ should generally be greater than 25° C.

Illustrative examples of suitable cross-linkable groups include but are not limited to hydride, acetoxy, alkoxy, amino, anhydride, aryloxy, carboxy, enoxy, epoxy, halide, isocyano, olefinic, and oxine. In more preferred embodiments, such polymeric starting material includes terminal monomers (also referred to as endcaps) that are either the same or different from the one or more monomers that comprise the polymeric starting material but include at least one cross-linkable group. In other words, the terminal monomers begin and end the polymeric starting material and include at least one cross-linkable group as part of its structure. Although it is not necessary for the practice of the present invention, the mechanism for cross-linking the polymeric starting material preferably is different than the mechanism for the stimulus-induced polymerization of the components that comprise the refraction modulating composition. For example, if the refraction modulating composition is polymerized by photoinduced polymerization, then it is preferred that the polymeric starting materials have cross-linkable groups that are polymerized by any mechanism other than photoinduced polymerization.

An especially preferred class of polymeric starting materials for the formation of the first polymer matrix is polysiloxanes (also known as "silicones") endcapped with a terminal monomer which includes a cross-linkable group selected from the group consisting of acetoxy, amino, alkoxy, halide, hydroxy, and mercapto. Because silicone IOLs tend to be flexible and foldable, generally smaller incisions may be used during the IOL implantation procedure. An example of an especially preferred polymeric starting materials are vinyl endcapped dimethylsiloxane diphenylsiloxane copolymer, silicone resin, and silicone hydride crosslinker that are crosslinked via an addition polymerization by platinum catalyst to form the silicone matrix. Other such examples may be found in U.S. Pat. No. 5,236,970, U.S. Pat. No. 5,376,694, U.S. Pat. No. 5,278,258, U.S. Pat. No. 5,444,106, and others similar to the described formulations, which are hereby incorporated herein by reference.

The MC that is used in fabricating IOLs is as described above except that it has the additional requirement of biocompatibility. The MC is capable of stimulus-induced polymerization and may be a single component or multiple components so long as: (i) it is compatible with the formation of the first polymer matrix; (ii) it remains capable of stimulus-induced polymerization after the formation of the first polymer matrix; and (iii) it is freely diffusible within the first polymer matrix. In general, the same type of monomers that are used to form the first polymer matrix may be used as components of the refraction modulating composition. However, because of the requirement that the MC monomers must be diffusible within the first polymer matrix, the MC monomers generally tend to be smaller (i.e., have lower molecular weights) than the first polymer matrix. In addition to the one or more monomers, the MC may include other components such as initiators and sensitizers that facilitate the formation of the second polymer network.

In preferred embodiments, the stimulus-induced polymerization is photopolymerization. In other words, the one or more monomers that comprise the refraction modulating composition each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the refraction modulating composition includes a photoinitiator (any compound used to generate free radicals) either alone or in the presence of a sensitizer. Examples of suitable photoinitiators include acetophenones (e.g., substituted haloacetophenones, and diethoxyacetophenone); 2,4-dichloromethyl-1,3,5-trazines; benzoin methyl ether; and o-benzoyl oximino ketone. Examples of suitable sensitizers include p-(dialkyiamino) aryl aldehyde; N-alkylindolylidene; and bis[p-(dialkylamino)benzylidene]ketone.

Because of the preference for flexible and foldable IOLs, an especially preferred class of MC monomers is polysiloxanes endcapped with a terminal siloxane moiety that includes a photopolymerizable group. An illustrative representation of such a monomer is:

$$X—Y—X^1$$

wherein Y is a siloxane which may be a monomer, a homopolymer or a copolymer formed from any number of siloxane units, and X and $X^1$ may be the same or different and are each independently a terminal siloxane moiety that includes a photopolymerizable group. An illustrative example of Y includes:

 and

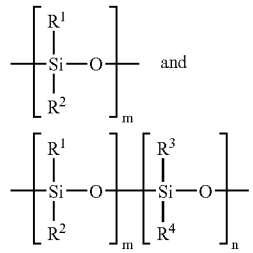

wherein: m and n are independently each an integer and $R^1$, $R^2$, $R^3$, and $R^4$ are independently each hydrogen, alkyl (primary, secondary, tertiary, cyclo), aryl, or heteroaryl. In preferred embodiments, $R^1$, $R^2$, $R^3$, and $R^4$ are $C_1$-$C_{10}$ alkyl or phenyl. Because MC monomers with a relatively high aryl content have been found to produce larger changes in the refractive index of the inventive lens, it is generally preferred that at least one of $R^1$, $R^2$, $R^3$, and $R^4$ is an aryl, particularly phenyl. In more preferred embodiments, $R^1$, $R^2$, and $R^3$ are the same and are methyl, ethyl or propyl and $R^4$ is phenyl.

Illustrative examples of X and $X^1$ (or $X^1$ and X depending on how the MC polymer is depicted) are:

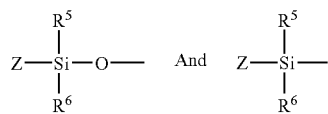

respectively wherein:

$R^5$ and $R^6$ are independently each hydrogen, alkyl, aryl, or heteroaryl; and Z is a photopolymerizable group.

In preferred embodiments $R^5$ and $R^6$ are independently each $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ are methyl, ethyl, or propyl and Z is a photopolymerizable group that includes an acrylate or methacrylate moiety.

In especially preferred embodiments, a MC monomer is of the following formula:

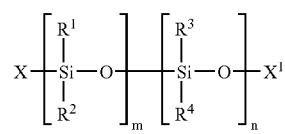

wherein X and $X^1$ are the same as $R^1$, $R^2$, $R^3$, and $R^4$ areas defined previously. Illustrative examples of such MC monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one or more cyclic siloxanes in the presence of triflic acid has been found to be a particularly efficient method of making one class of inventive MC monomers. Briefly, the method comprises contacting a cyclic siloxane with a compound of the formula:

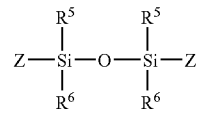

in the presence of triflic acid wherein $R^5$ and $R^6$, and Z are as defined previously. The cyclic siloxane may be a cyclic siloxane monomer, momopolymer, or copolymer. Alternatively, more than one cyclic siloxane may be used. For example, a cyclic dimethylsiloxane tetrameter and a cyclic methyl-phenylsiloxane trimer are contacted with bis-methacryloxypropyltetramethyldisiloxane in the presence of triflic acid to form a dimethylsiloxane methyl-phenylsiloxane copolymer that is endcapped with a methacryloxylpropyl-dimethylsilane group, an especially preferred MC monomer.

In addition to the silicone-based MCs described above, acrylate-based MC can also be used in the practice of the invention. The acrylate-based macromers of the invention have the general structure:

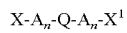

or

wherein Q is an acrylate moiety capable of acting as an initiator for Atom Transfer Radical Polymerization ("ATRP"), A and $A^1$ have the general structure:

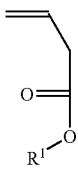

wherein $R^1$ is selected from the group comprising alkyls, halogenated alkyls, aryls and halogenated aryls and X and $X^1$ are groups containing photopolymerizable moieties and m and n are integers.

In one embodiment the acrylate based MC has the formula:

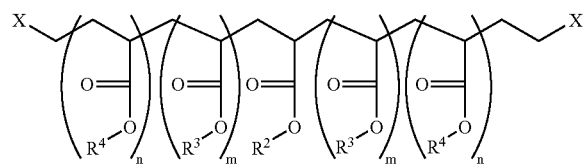

wherein $R^2$ is selected from the group comprising alkyls and halogenated alkyls $R^3$ and $R^4$ are different and are selected from the group consisting of alkyls, halogenated alkyls, aryls and halogenated aryls.

When the optical element is formed, it is then positioned in the area where it is to be used. For an intraocular lens, this means implantation into the eye using known procedures. Once the element is in place and is allowed to adjust to its environment, it is then possible to modify the optical properties of the element through exposure to an external stimulus.

The nature of the external stimulus can vary but it must be capable of reducing polymerization of the MC without adversely affecting the properties of the optical element. Typical external stimuli that can be used in practice of the invention include heat and light, with light preferred. In the case of intraocular lenses, ultraviolet or infrared radiation is preferred with ultraviolet light most preferred.

When the element is exposed to the external stimulus, the MC polymerization forms a second polymer matrix, interspersed with the first polymer matrix. When the polymerization is localized or when only a portion of the MC is polymerized, there is a difference in the chemical potential between the reacted and unreacted regions of the lens. The MC then migrates within the element to reestablish the thermodynamic equilibrium within the optical element.

The formation of the second polymer matrix and the re-distribution of the MC can each affect the optical properties of the element. For example, the formation of the second polymer matrix can cause changes in the refractive index of the element. The migration of the modifying compound can alter the overall shape of the element, further affecting the optical properties by changing the radii of curvatures of the optical element.

The inventive IOLs may be fabricated with any suitable method that results in a first polymer matrix with one or more components which comprise the refraction modulating composition dispersed therein, and wherein the refraction modulating composition is capable of stimulus-induced polymerization to form a second polymer matrix. In general, the method for making an inventive IOL is the same as that for making an inventive optical element. In one embodiment, the method comprises mixing a first polymer matrix composition with a refraction modulating composition to form a reaction mixture;

placing the reaction mixture into a mold;

polymerizing the first polymer matrix composition to form said optical element; and, removing the optical element from the mold.

The type of mold that is used will depend on the optical element being made. For example, if the optical element is a prism, then a mold in the shape of a prism is used. Similarly, if the optical element is an intraocular lens, then an intraocular lens mold is used and so forth. As described previously, the first polymer matrix composition comprises one or more monomers for forming the first polymer matrix and optionally includes any number of formulation auxiliaries that either modulate the polymerization reaction or improve any property (whether or not related to the optical characteristic) of the optical element. Similarly, the refraction modulating composition comprises one or more components that together are capable of stimulus-induced polymerization to form the second polymer matrix. Because flexible and foldable intraocular lenses generally permit smaller incisions, it is preferred that both the first polymer matrix composition and the refraction modulating composition include one or more silicone-based or low T.sub.g acrylic monomers when the inventive method is used to make IOLs.

A key advantage of the intraocular lens of the present invention is that an IOL property may be modified after implantation within the eye. For example, any errors in the power calculation due to imperfect corneal measurements andor variable lens positioning and wound healing may be modified in a post surgical outpatient procedure.

In addition to the change in the IOL refractive index, the stimulus-induced formation of the second polymer matrix has been found to affect the IOL power by altering the lens curvature in a predictable manner. As a result, both mechanisms may be exploited to modulate an IOL property, such as power, after it has been implanted within the eye. In general, the method for implementing an inventive IOL having a first polymer matrix and a refraction modulating composition dispersed therein, comprises:

(a) exposing at least a portion of the lens to a stimulus whereby the stimulus induces the polymerization of the refraction modulating composition.

If after implantation and wound healing, no IOL property needs to be modified, then the exposed portion is the entire lens. The exposure of the entire lens will lock in the then existing properties of the implanted lens.

However, if a lens characteristic such as its power needs to be modified, then only a portion of the lens (something less than the entire lens) would be exposed. In one embodiment, the method of implementing the inventive IOL farther comprises:

(b) waiting an interval of time; and (c) re-exposing the portion of the lens to the stimulus.

This procedure generally will induce the further polymerization of the refraction modulating composition within the exposed lens portion. Steps (b) and (c) may be repeated any number of times until the intraocular lens (or optical element) has reached the desired lens characteristic. At this point, the method may further include the step of exposing the entire lens to the stimulus to lock-in the desired lens property.

In another embodiment wherein a lens property needs to be modified, a method for implementing an inventive IOL comprises:

(a) exposing a first portion of the lens to a stimulus whereby the stimulus induces the polymerization of the refraction modulating composition; and (b) exposing a second portion of the lens to the stimulus.

The first lens portion and the second lens portion represent different regions of the lens although they may overlap. Optionally, the method may include an interval of time between the exposures of the first lens portion and the second lens portion. In addition, the method may further comprise re-exposing the first lens portion andor the second lens portion any number of times (with or without an interval of time between exposures) or may further comprise exposing additional portions of the lens (e.g., a third lens portion, a fourth lens portion, etc.). Once the desired property has been reached, then the method may further include the step of exposing the entire lens to the stimulus to lock-in the desired lens property.

It is possible to localize the exposure of the optical element to the external stimulus in such a manner to create zones within the element with different optical properties. In one embodiment, it is possible to create an intraocular lens that can be transferred into a multifocal lens after implantation. This is accomplished by exposing the lens to different amounts of external stimulus to create zone(s) having different optical properties.

In the case of a multifocal intraocular lens, various methods can be used to create the lenses. In its simplest form, it can be of the bull's eye configuration comprising an add or subtract zone in the central 1 to 3 mm zone of the lens and the resultant lens base power outside this zone. The lenses can be divided into separate zones, alternating zones or overlapping zones. For example, separate zones would include outer and inner zones. A Fresnel lens is an example of alternating zones.

Overlapping zones are particularly useful in diffractive optical elements such as holograms, binary optic, kinoforms and holographic optical elements.

In the case of an intraocular lens, it is possible to form a lens, implant it, and then form different zones or regions in the lens having different optical properties. By exposing different areas of the lens to different magnitudes and spatial profiles of external stimuli, different optical zones can be created. For example, the lens body can be divided into central zone, inner and outer annular near zones, and annular far zones. In this embodiment, the central zone is circular and the peripheries of the annular zones are circular. The annular zones circumscribe the central zone and the zones are contiguous. The zones are concentric and coaxial with the lens body.

The zones are used in describing the vision correction power of the lens, and they are arbitarily defined. Thus, the peripheries of the zones and the numbers of zones may be selected as desired.

The following examples are offered by way of example and are not intended to limit the scope of the invention in any manner.

EXAMPLE 1

Materials comprising various amounts of (a) poly-dimethylsiloxane endcapped with diacetoxymethylsilane ("PDMS") (36000 g/mol), (b) dimethylsiloxane-diphenylsiloxane copolymer endcapped with vinyl-dimethyl silane ("DMDPS ") (15,500 g/mol), and (c) a UV-photoinitiator, 2,2-dimethoxy-2-phenylacetophenone ("DMPA") as shown by Table 1 were made and tested. PDMS is the monomer which forms first polymer matrix, and DMDPS and DMPA together comprise the refraction modulating composition.

TABLE 1

| | PDMS (wt. %) | DMDPS (wt. %) | DMPA (wt. %).sup.a |
|---|---|---|---|
| 1 | 90 | 10 | 1.5 |
| 2 | 80 | 20 | 1.5 |
| 3 | 75 | 25 | 1.5 |
| 4 | 70 | 30 | 1.5 |

.sup.a wt % with respect to DMDPS.

Briefly, appropriate amounts of PMDS (Gelest DMS-D33; 36000 g/mol), DMDPS (Gelest PDV-0325; 3.0-3.5 mole % diphenyl, 15,500 g/mol), and DMPA (Acros; 1.5 wt % with respect to DMDPS) were weighed together in an aluminum pan, manually mixed at room temperature until the DMPA dissolved, and degassed under pressure (5 mtorr) for 2-4 minutes to remove air bubbles. Photosensitive prisms were fabricated by pouring the resulting silicone composition into a mold made of three glass slides held together by scotch tape in the form of a prism and sealed at one end with silicone caulk. The prisms are about 5 cm long and the dimensions of the three sides are about 8 mm each. The PDMS in the prisms was moisture cured and stored in the dark at room temperature for a period of 7 days to ensure that the resulting first polymer matrix was non-tacky, clear, and transparent.

The amount of photoinitiator (1.5 wt. %) was based on prior experiments with fixed RMC monomer content of 25% in which the photoinitiator content was varied. Maximal refractive index modulation was observed for compositions containing 1.5% and 2 wt. % photoinitiator while saturation in refractive index occurred at 5 wt. %.

EXAMPLE 2

Synthesis RMC Monomers

As illustrated by Scheme 1, commercially available cyclic dimethylsiloxane tetramer ("$D_4$"), cyclic methylphenylsiloxane trimer ("$D_3$") in various ratios were ring-opened by triflic acid and bis-methacryloxylpropyltetramethyldisiloxane ("MPS") were reacted in a one pot synthesis. U.S. Pat. No. 4,260,725; Kunzler, J. F., Trends in Polymer Science, 4: 52-59 (1996); Kunzler et al. J. Appl. Poly. Sci., 55: 611-619 (1995); and Lai et al., J. Poly. Sci. A. Poly. Chem., 33: 1773-1782 (1995).

Scheme 1

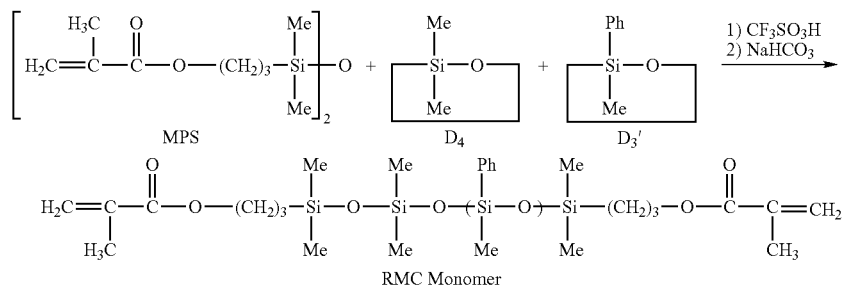

Briefly, appropriate amounts of MPS, $D_4$, and $D_3'$ were stirred in a vial for 1.5-2 hours. An appropriate amount of triflic acid was added and the resulting mixture was stirred for another 20 hours at room temperature. The reaction mixture was diluted with hexane, neutralized (the acid) by the addition of sodium bicarbonate, and dried by the addition of anhydrous sodium sulfate. After filtration and rotovaporation of hexane, the RMC monomer was purified by further filtration through an activated carbon column. The RMC monomer was dried at 5 mtorr of pressure between 70-80° C. for 12-18 hours.

The amounts of phenyl, methyl, and endgroup incorporation were calculated from $^1$H-NMR spectra that were run in deuterated chloroform without internal standard tetramethylsilane ("TMS"). Illustrative examples of chemical shifts for some of the synthesized RMC monomers follows. A 1000 g/mole RMC monomer containing 5.58 mole % phenyl (made by reacting: 4.85 g (12.5 mmole) of MPS; 1.68 g (4.1 mmole) of $D_3'$; 5.98 g (20.2 mmole) of $D_4$; and 108 µl (1.21 mmole) of triflic acid: δ=7.56-7.5 ppm (m, 2H) aromatic, δ=7.32-7.33 ppm (m, 3H) aromatic, δ=6.09 ppm (d, 2H) olefinic, δ=5.53 ppm (d, 2H) olefinic, δ=4.07-4.10 ppm (t, 4H) —O—C$\underline{H}_2$CH$_2$CH$_2$—, δ=1.93 ppm (s, 6H) methyl of methacrylate, δ=1.65-1.71 ppm (m, 4H) —O—CH$_2$C$\underline{H}_2$CH$_2$—, δ=0.54-0.58 ppm (m, 4H) —O—CH$_2$CH$_2$C$\underline{H}_2$—Si, δ=0.29-0.30 ppm (d, 3H), C$\underline{H}_3$—Si-Phenyl, δ=0.04-0.08 ppm (s, 50 H) (C$\underline{H}_3$)$_2$Si of the backbone.

A 2000 g/mole RMC monomer containing 5.26 mole % phenyl (made by reacting: 2.32 g (6.0 mmole) of MPS; 1.94 g (4.7 mmole) of $D_3'$; 7.74 g (26.1 mmole) of $D_4$; and 136 µl (1.54 mmole) of triflic acid: δ=7.54-7.58 ppm (m, 4H) aromatic, δ=7.32-7.34 ppm (m, 6H) aromatic, δ=6.09 ppm (d, 2H) olefinic, δ=5.53 ppm (d, 2H) olefinic, δ=4.08-4.11 ppm (t, 4H) —O—C$\underline{H}_2$CH$_2$CH$_2$—, δ=1.94 ppm (s, 6H) methyl of methacrylate, δ=1.67-1.71 ppm (m, 4H) —O—C H$_2$CH$_2$CH$_2$—, δ=0.54-0.59 ppm (m, 4H) —O—CH$_2$CH$_2$C H$_2$—Si, δ=0.29-0.31 ppm (m, 6H), C$\underline{H}_3$—Si-Phenyl, δ=0.04-0.09 ppm (s, 112H) (C$\underline{H}_3$)$_2$ Si of the backbone.

A 4000 g/mole RMC monomer containing 4.16 mole % phenyl (made by reacting: 1.06 g (2.74 mmole) of MPS; 1.67 g (4.1 mmole) of $D_3'$; 9.28 g (31.3 mmole) of $D_4$; and 157 µl (1.77 mmole) of triflic acid: $D_3'$=7.57-7.60 ppm (m, 8H) aromatic, δ=7.32-7.34 ppm (m, 6H) aromatic, δ=6.10 ppm (d, 2H) olefinic, δ=5.54 ppm (d, 2H) olefinic, δ=4.08-4.12 ppm (t, 4H) —O—CHhd2CH$_2$CH$_2$—, δ=1.94 ppm (s, 6H) methyl of methacrylate, δ=1.65-1.74 ppm (m, 4H) —O—CH$_2$CH$_2$CH$_2$—, δ=0.55-0.59 ppm (m, 4H) —O—C H$_2$CH$_2$—Si, δ=0.31 ppm (m, 11H), C$\underline{H}_3$—Si-Phenyl, δ=0.07-0.09 ppm (s, 272 H) (C$\underline{H}_3$)$_2$ Si of the backbone.

Similarly, to synthesize dimethylsiloxane polymer without any methylphenylsiloxane units and endcapped with methyacryloxypropyl dimethylsilane, the ratio of $D_4$ to MPS was varied without incorporating $D_3'$.

Molecular weights were calculated by $^1$H-NMR and by gel permeation chromatography ("GPC"). Absolute molecular weights were obtained by universal calibration method using polystyrene and poly(methyl methacrylate) standards. Table 2 shows the characterization of other RMC monomers synthesized by the triflic acid ring opening polymerization.

TABLE 2

| | Mole % Phenyl | Mole % Methyl | Mole % Methacrylate | Mn (NMR) | Mn (GPC) | $^nD$ |
|---|---|---|---|---|---|---|
| A | 6.17 | 87.5 | 6.32 | 1001 | 946 | 1.44061 |
| B | 3.04 | 90.8 | 6.16 | 985 | 716 | 1.43188 |
| C | 5.26 | 92.1 | 2.62 | 1906 | 1880 | — |
| D | 4.16 | 94.8 | 1.06 | 4054 | 4200 | 1.42427 |
| E | 0 | 94.17 | 5.83 | 987 | 1020 | 1.42272 |
| F | 0 | 98.88 | 1.12 | 3661 | 4300 | 1.40843 |

At 10-40 wt %, these RMC monomers of molecular weights 1000 to 4000 g/mol with 3-6.2 mole % phenyl content are completely miscible, biocompatible, and form optically clear prisms and lenses when incorporated in the silicone matrix. RMC monomers with high phenyl content (4-6 mole %) and low molecular weight (1000-4000 g/mol) resulted in increases in refractive index change of 2.5 times and increases in speeds of diffusion of 3.5 to 5.0 times compared to the RMC monomer used in Table 1 (dimethylsiloxane-diphenylsiloxane copolymer endcapped with vinyldimethyl silane ("DMDPS") (3-3.5 mole % diphenyl content, 15500 g/mol). These RMC monomers were used to make optical elements comprising: (a) polydimethylsiloxane endcapped with diacetoxymethylsilane ("PDMS") (36000 g/mol), (b) dimethylsiloxane methylphenylsiloxane copolymer that is endcapped with a methacryloxylpropyldimethylsilane group, and (c) 2,2-dimethoxy-2-phenylacetophenone ("DMPA"). Note that component (a) is the monomer that forms the first polymer matrix and components (b) and (c) comprise the refraction modulating composition.

EXAMPLE 3

Fabrication of Intraocular Lenses ("IOL")

An intraocular mold was designed according to well-accepted standards. See e.g., U.S. Pat. Nos. 5,762,836; 5,141,678; and 5,213,825. Briefly, the mold is built around two plano-concave surfaces possessing radii of curvatures of −6.46 mm and/or −12.92 mm, respectively. The resulting lenses are 6.35 mm in diameter and possess a thickness ranging from 0.64 mm, 0.98 mm, or 1.32 mm depending upon the combination of concave lens surfaces used. Using two different radii of curvatures in their three possible combinations and assuming a nominal refractive index of 1.404 for the IOL composition, lenses with pre-irradiation powers of 10.51 D (62.09 D in air), 15.75 D (92.44 in air), and 20.95 D (121.46 D in air) were fabricated.

EXAMPLE 4

Stability of Compositions Against Leaching

Three IOLs were fabricated with 30 and 10 wt % of RMC monomers B and D incorporated in 60 wt % of the PDMS matrix. After moisture curing of PDMS to form the first polymer matrix, the presence of any free RMC monomer in the aqueous solution was analyzed as follows. Two out of three lenses were irradiated three times for a period of 2 minutes using 340 nm light, while the third was not irradiated at all. One of the irradiated lenses was then locked by exposing the entire lens matrix to radiation. All three lenses were mechanically shaken for 3 days in 1.0 M NaCl solution. The NaCl solutions were then extracted by hexane and analyzed by $^1$H-NMR. No peaks due to the RMC monomer were observed in the NMR spectrum. These results suggest that the RMC monomers did not leach out of the matrix into the aqueous phase in all three cases. Earlier studies on a vinyl endcapped silicone RMC monomer showed similar results even after being stored in 1.0 M NaCl solution for more than one year.

EXAMPLE 5

Toxicological Studies in Rabbit Eyes

Sterilized, unirradiated and irradiated silicone IOLs (fabricated as described in Example 3) of the present invention and a sterilized commercially available silicone IOL were implanted in albino rabbit eyes. After clinically following the eyes for one week, the rabbits were sacrificed. The extracted eyes were enucleated, placed in formalin and studied histopathologically. There is no evidence of corneal toxicity, anterior segment inflammation, or other signs of lens toxicity.

EXAMPLE 6

Irradiation of Silicone Prisms

Because of the ease of measuring refractive index change (Δn) and percent net refractive index change (% Δn) of prisms, the inventive formulations were molded into prisms for irradiation and characterization. Prisms were fabricated by mixing and pouring (a) 90-60 wt % of high Mn PDMS, (b) 10-40 wt % of RMC monomers in Table 2, and (c) 0.75 wt % (with respect to the RMC monomers) of the photoinitiator DMPA into glass molds in the form of prisms 5 cm long and 8.0 mm on each side. The silicone composition in the prisms was moisture cured and stored in the dark at room temperature for a period of 7 days to ensure that the final matrix was non-tacky, clear and transparent.

Figure 11:
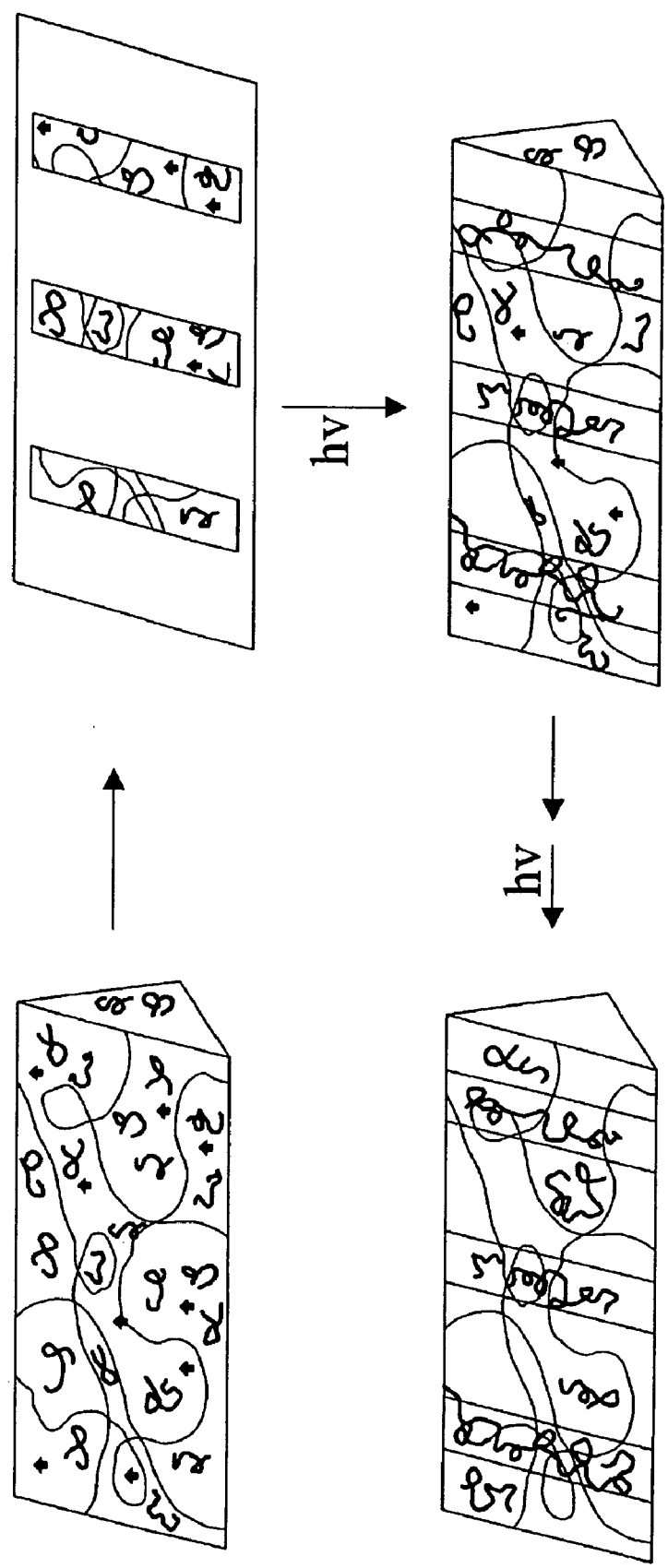
FIG. 11 illustrates the prism irradiation procedure that is used to quantify the refractive index changes after being exposed to various amounts of irradiation
Figure 12:
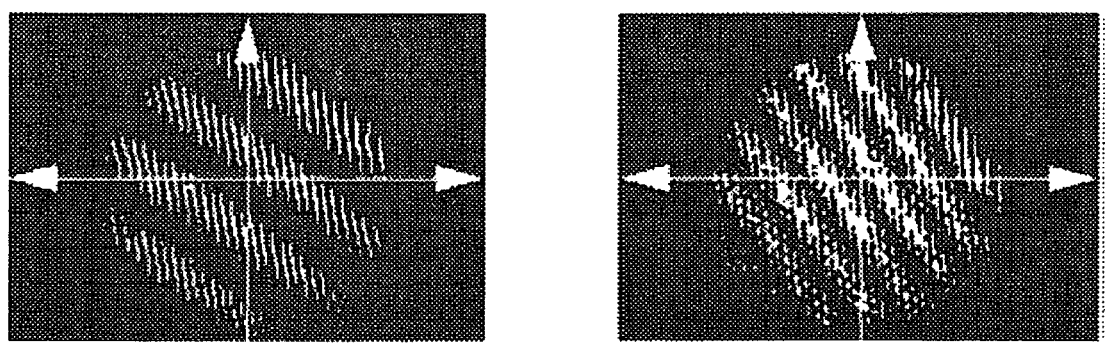
FIG. 12 shows unfiltered moiré fringe patterns of an inventive IOL. The angle between the two Ronchi rulings was set at 12° and the displacement distance between the first and second moiré patterns was 4.92 mm.

Two of the long sides of each prism were covered by a black background while the third was covered by a photomask made of an aluminum plate with rectangular windows (2.5 mm.times.10 mm). Each prism was exposed to a flux of 1.2 mW/cm$^2$ of a collimated 340 nm light (peak absorption of the photoinitiator) from a 1000 W Xe:Hg arc lamp for various time periods. The ANSI guidelines indicate that the maximum permissible exposure ("MPE") at the retina using 340 nm light for a 10-30000 s exposure is 1000 mJ/cm$^2$. Criteria for Exposure of Eye and Skin. American National Standard Z136.1:31-42 (1993). The single dose intensity 1.2 mW/cm$^2$ of 340 nm light for a period of 2 minutes corresponds to 144 mJ/cm$^2$ which is well within the ANSI guidelines. In fact, even the overall intensity for three exposures (432 mJ/cm$^2$) is well within the ANSI guidelines. FIG. 11 is an illustration of the prism irradiation procedure.

The prisms were subject to both (i) continuous irradiation—one-time exposure for a known time period, and (ii) "staccato" irradiation—three shorter exposures with long intervals between them. During continuous irradiation, the refractive index contrast is dependent on the crosslinking density and the mole % phenyl groups, while in the interrupted irradiation, RMC monomer diffusion and further crosslinking also play an important role. During staccato irradiation, the RMC monomer polymerization depends on the rate of propagation during each exposure and the extent of interdiffusion of free RMC monomer during the intervals between exposures. Typical values for the diffusion coefficient of oligomers (similar to the 1000 g/mole RMC monomers used in the practice of the present invention) in a silicone matrix are on the order of $10^{-6}$ to $10^{-7}$ /cm$^2$/s. In other words, the inventive RMC monomers require approximately 2.8 to 28 hours to diffuse 1 mm (roughly the half width of the irradiated bands). The distance of a typical optical zone in an IOL is about 4 to about 5 mm across. However, the distance of the optical zone may also be outside of this range. After the appropriate exposures, the prisms were irradiated without the photomask (thus exposing the entire matrix) for 6 minutes using a medium pressure mercury-arc lamp. This polymerized the remaining silicone RMC monomers and thus "locked" the refractive index of the prism in place. Notably, the combined total irradiation of the localized exposures and the "lock-in" exposure was still within ANSI guidelines.

EXAMPLE 7

Prism Dose Response Curves

Inventive prisms fabricated from RMC monomers described by Table 2 were masked and initially exposed for 0.5, 1, 2, 5, and 10 minutes using 1.2 mW/cm$^2$ of the 340 nm line from a 1000 W Xe:Hg arc lamp. The exposed regions of the prisms were marked, the mask detached and the refractive index changes measured. The refractive index modulation of the prisms was measured by observing the deflection of a sheet of laser light passed through the prism. The difference in deflection of the beam passing through the exposed and unexposed regions was used to quantify the refractive index change (Δn) and the percentage change in the refractive index (% Δn).

After three hours, the prisms were remasked with the windows overlapping with the previously exposed regions and irradiated for a second time for 0.5, 1, 2, and 5 minutes (total time thus equaled 1, 2, 4, and 10 minutes respectively). The masks were detached and the refractive index changes measured. After another three hours, the prisms were exposed a third time for 0.5, 1, and 2 minutes (total time thus equaled 1.5, 3, and 6 minutes) and the refractive index changes were measured. As expected, the % Δn increased with exposure time for each prism after each exposure resulting in prototypical dose response curves. Based upon these results, adequate RMC monomer diffusion appears to occur in about 3 hours for 1000 g/mole RMC monomer.

All of the RMC monomers (B-F) except for RMC monomer A resulted in optically clear and transparent prisms before and after their respective exposures. For example, the largest % Δn for RMC monomers B, C, and D at 40 wt % incorporation into 60 wt % FPMC were 0.52%, 0.63% and 0.30% respectively which corresponded to 6 minutes of total exposure (three exposures of 2 minutes each separated by 3 hour intervals for RMC monomer B and 3 days for RMC monomers C and D). However, although it produced the largest change in refractive index (0.95%), the prism fabricated from RMC monomer A (also at 40 wt % incorporation into 60 wt % FPMC and 6 minutes of total exposure—three exposures of 2 minutes each separated by 3 hour intervals) turned somewhat cloudy. Thus, if RMC monomer A were used to fabricate an IOL, then the RMC must include less than 40 wt % of RMC monomer A or the % Δn must be kept below the point where the optical clarity of the material is compromised.

A comparison between the continuous and staccato irradiation for RMC A and C in the prisms shows that lower % Δn values occurs in prisms exposed to continuous irradiation as compared to those observed using staccato irradiations. As indicated by these results, the time interval between exposures (which is related to the amount of RMC diffusion from the unexposed to exposed regions) may be exploited to precisely modulate the refractive index of any material made from the inventive polymer compositions.

Exposure of the entire, previously irradiated prisms to a medium pressure Hg arc lamp polymerized any remaining free RMC, effectively locking the refractive index contrast. Measurement of the refractive index change before and after photolocking indicated no further modulation in the refractive index.

EXAMPLE 8

Optical Characterization of IOLS

Talbot interferometry and the Ronchi test were used to qualitatively and quantitatively measure any primary optical aberrations (primary spherical, coma, astigmatism, field curvature, and distortion) present in pre- and post-irradiated lenses as well as quantifying changes in power upon photopolymerization.

In Talbot interferometry, the test IOL is positioned between the two Ronchi rulings with the second grating placed outside the focus of the IOL and rotated at a known angle, θ, with respect to the first grating. Superposition of the autoimage of the first Ronchi ruling ($p_1$=300 lines/inch) onto the second grating ($p_2$=150 lines/inch) produces moiré fringes inclined at an angle, $α_1$. A second moiré fringe pattern is constructed by axial displacement of the second Ronchi ruling along the optic axis a known distance, d, from the test lens. Displacement of the second grating allows the autoimage of the first Ronchi ruling to increase in magnification causing the observed moiré fringe pattern to rotate to a new angle, $α_2$. Knowledge of moiré pitch angles permits determination of the focal length of the lens (or inversely its power) through the expression:

$$f = \frac{p_1}{p_2} d \left( \frac{1}{\tan\alpha_2 \sin\theta + cps\theta} - \frac{1}{\tan\alpha_1 \sin\theta + \cos\theta} \right)^{-1}$$

To illustrate the applicability of Talbot interferometry to this work, moiré fringe patterns of one of the inventive, pre-irradiated IOLs (60 wt % PDMS, 30 wt % RMC monomer B, wt % RMC monomer D, and 0.75% DMPA relative to the two RMC monomers) measured in air is presented in FIG. 3. Each of the moiré fringes was fitted with a least squares fitting algorithm specifically designed for the processing of moiré patterns. The angle between the two Ronchi rulings was set at 12°, the displacement between the second Ronchi ruling between the first and second moiré fringe patterns was 4.92 mm, and the pitch angles of the moiré fringes, measured relative to an orthogonal coordinate system defined by the optic axis of the instrument and crossing the two Ronchi rulings at 90°, were $α_1$, = −33.2°±0.30° and $α_2$=−52.7°±0.40°. Substitution of these above equation results in a focal length of 10.71±0.50 mm (power=93.77±4.6 D).

Figure 13:
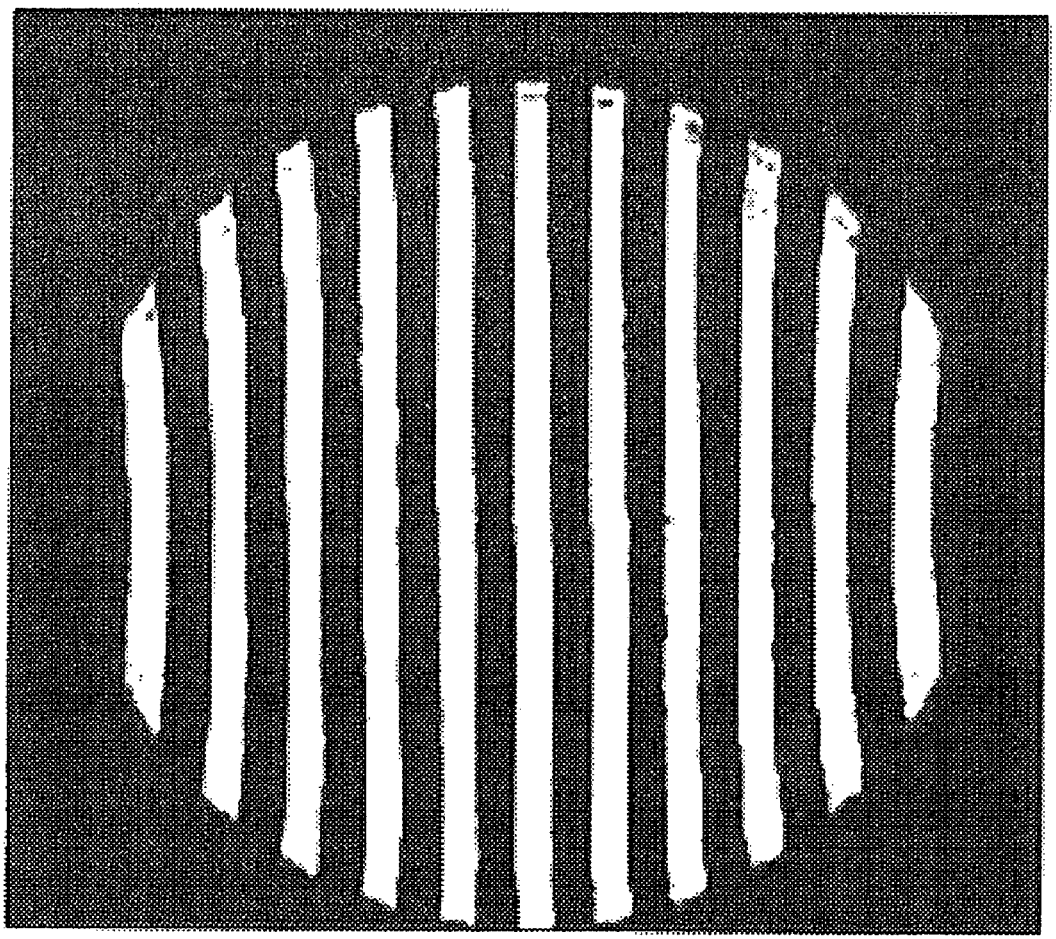
FIG. 13 is a Ronchigram of an inventive IOL. The Ronchi pattern corresponds to a 2.6 mm central region of the lens.

Optical aberrations of the inventive IOLs (from either fabrication or from the stimulus-induced polymerization of the RMC components) were monitored using the "Ronchi Test" which involves removing the second Ronchi ruling from the Talbot interferometer and observing the magnified autoimage of the first Ronchi ruling after passage though the test IOL. The aberrations of the test lens manifest themselves by the geometric distortion of the fringe system (produced by the Ronchi ruling) when viewed in the image plane. A knowledge of the distorted image reveals the aberration of the lens. In general, the inventive fabricated lenses (both pre and post irradiation treatments) exhibited sharp, parallel, periodic spacing of the interference fringes indicating an absence of the majority of primary-order optical aberrations, high optical surface quality, homogeneity of n in the bulk, and constant lens power. FIG. 13 is an illustrative example of a Ronchigram of an inventive, pre-irradiated IOL that was fabricated from 60 wt % PDMS, 30 wt % RMC monomer B, 10 wt % RMC monomer D, and 0.75% of DMPA relative to the 2 RMC monomers.

The use of a single Ronchi ruling may also be used to measure the degree of convergence of a refracted wavefront (i.e., the power). In this measurement, the test IOL is placed in contact with the first Ronchi ruling, collimated light is brought incident upon the Ronchi ruling, and the lens and the magnified autoimage is projected onto an observation screen. Magnification of the autoimage enables measurement of the curvature of the refracted wavefront by measuring the spatial frequency of the projected fringe pattern. These statements are quantified by the following equation:

$$P_v = \frac{1000}{L}\left(1 + \frac{d_s}{d}\right)$$

wherein $P_v$ is the power of the lens expressed in diopters, L is the distance from the lens to the observing plane, $d_s$, is the magnified fringe spacing of the first Ronchi ruling, and d is the original grating spacing.

EXAMPLE 9

Power Changes from Photopolymerization of the Inventive IOLS

An inventive IOL was fabricated as described by Example 3 comprising 60 wt % PDMS ($n_D$=1.404), 30 wt % of RMC monomer B (n.sub.D=1.4319), 10 wt % of RMC monomer D ($n_D$=1.4243), and 0.75 wt % of the photoinitiator DMPA relative to the combined weight percents of the two RMC monomers. The IOL was fitted with a 1 mm diameter photomask and exposed to 1.2 mW/cm² of 340 nm collimated light from a 1000 W Xe:Hg arc lamp for two minutes. The irradiated lens was then placed in the dark for three hours to permit polymerization and RMC monomer diffusion. The IOL was photolocked by continuously exposing the entire for six minutes using the aforementioned light conditions. Measurement of the moiré pitch angles followed by substitution into equation 1 resulted in a power of 95.1±2.9 D (f=10.52±0.32 mm) and 104.1±3.6 D (f=9.61 mm±0.32 mm) for the unirradiated and irradiated zones, respectively.

The magnitude of the power increase was more than what was predicted from the prism experiments where a 0.6% increase in the refractive index was routinely achieved. If a similar increase in the refractive index was achieved in the IOL, then the expected change in the refractive index would be 1.4144 to 1.4229. Using the new refractive index (1.4229) in the calculation of the lens power (in air) and assuming the dimensions of the lens did not change upon photopolymerization, a lens power of 96.71 D (f=10.34 mm) was calculated. Since this value is less than the observed power of 104.1±3.6 D, the additional increase in power must be from another mechanism.

Figure 14:
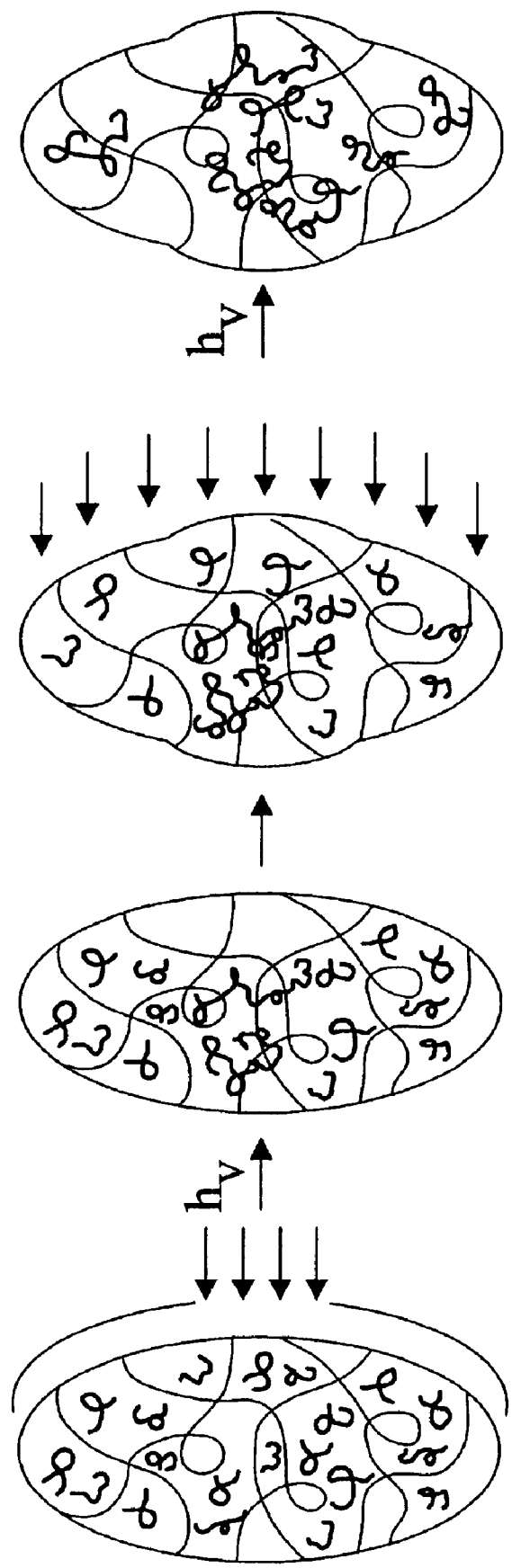
FIG. 14 is a schematic illustrating a second mechanism whereby the formation of the second polymer matrix modulates a lens property by altering lens shape.

Further study of the photopolymerized IOL showed that subsequent RMC monomer diffusion after the initial radiation exposure leads to changes in the radius of curvature of the lens. See e.g., FIG. 14. The RMC monomer migration from the unradiated zone into the radiated zone causes either or both of anterior and posterior surfaces of the lens to swell thus changing the radius of curvature of the lens. It has been determined that a 7% decrease in the radius of curvature for both surfaces is sufficient to explain the observed increase in lens power.

Figure 15:
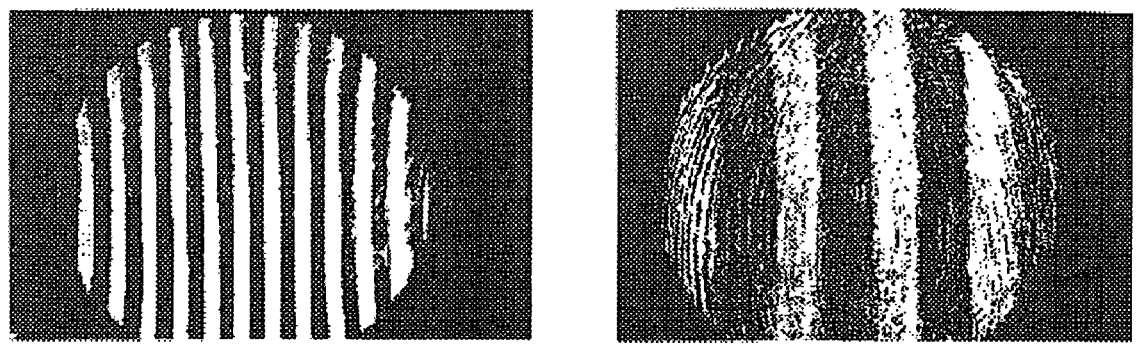
FIG. 15 are Ronchi interferograms of an IOL before and after laser treatment depicting approximately a +8.6 diopter change in lens power within the eye. The spacing of alternative light and dark bands is proportional to lens power.

The concomitant change in the radius of curvature was further studied. An identical IOL described above was fabricated. A Ronchi interferogram of the IOL is shown in FIG. 15a (left interferogram). Using a Talbot interferometer, the focal length of the lens was experimentally determined to be 10.52±0.30 mm (95.1±2.8 D). The IOL was then fitted with a 1nmm photomask and irradiated with 1.2 mW/cm² of 340 collimated light from a 1000 W Xe:Hg arc lamp continuously for 2.5 minutes. Unlike the previous IOL, this lens was not "locked in" three hours after irradiation. FIG. 15b (right interferogram) is the Ronchi interferogram of the lens taken six days after irradiation. The most obvious feature between the two interference patterns is the dramatic increase in the fringe spacing, which is indicative of an increase in the refractive power of the lens.

Measurement of the fringe spacings indicates an increase of approximately +38 diopters in air (f≈7.5 mm). This corresponds to a change in the order of approximately +8.6 diopters in the eye. Since most post-operative corrections from cataract surgery are within 2 diopters, this experiment indicates that the use of the inventive IOLS will permit a relatively large therapeutic window.

EXAMPLE 10

Photopolymerization Studies of Non-Phenyl-Containing IOLS

Inventive IOLs containing non-phenyl containing RMC monomers were fabricated to further study the swelling from the formation of the second polymer matrix. An illustrative example of such an IOL was fabricated from 60 wt % PDMS, 30 wt % RMC monomer E, 10 wt % RMC monomer F, and 0.75% DMPA relative to the two RMC monomers. The pre-irradiation focal length of the resulting IOL was 10.76 mm (92.94±2.21 D).

In this experiment, the light source was a 325 nm laser line from a He:Cd laser. A 1 mm diameter photomask was placed over the lens and exposed to a collimated flux of 0.75 mW/cm² at 325 nm for a period of two minutes. The lens was then placed in the dark for three hours. Experimental measurements indicated that the focal length of the IOL changed from 10.76 mm±0.0.25 mm (92.94 D±0.2.21 D) to 8.07 mm±0.74 mm (123.92 D±0.10.59 D) or a dioptric change of +30.98 D±10.82 D in air. This corresponds to an approximate change of +6.68 D in the eye. The amount of irradiation required to induce these changes is only 0.09 J/cm², a value well under the ANSI maximum permissible exposure ("MPE") level of 1.0 J/cm².

EXAMPLE 11

Monitoring for Potential IOL Changes from Ambient Light

The optical power and quality of the inventive IOLs were monitored to show that handling and ambient light conditions do not produce any unwanted changes in lens power. A 1 mm open diameter photomask was placed over the central region of an inventive IOL (containing 60 wt % PDMS, 30 wt % RMC monomer E, 10 wt % RMC momnomer F, and 0.75 wt % DMPA relative to the two RMC monomers), exposed to continuous room light for a period of 96 hours, and the spatial frequency of the Ronchi patterns as well as the moiré fringe angles were monitored every 24 hours. Using the method of moiré fringes, the focal length measured in the air of the lens immediately after removal from the lens mold is 10.87±0.23 mm (92.00 D±1.98 D) and after 96 hours apf exposure to ambient room light is 10.74 mm±0.25=mm (93.11 D±2.22 D). Thus, within the experimental uncertainty of the measurement, it is shown that ambient light does not induce any unwanted change in power. A comparison of the resulting Ronchi patterns showed no change in spatial frequency or quality of the interference pattern, confirming that exposure to room light does not affect the power or quality of the inventive IOLs.

EXAMPLE 12

Effect of the Lock in Procedure of an Irradiated IOL

An inventive IOL whose power had been modulated by irradiation was tested to see if the lock-in procedure resulted in further modification of lens power. An IOL fabricated from 60 wt % PDMS, 30 wt % RMC monomer E, 10 wt % RMC monomer F, and 0.75% DMPA relative to the two RMC monomers was irradiated for two minutes with 0.75 mW/cm² of the 325 nm laser line from a He:Cd laser and was exposed for eight minutes to a medium pressure Hg arc lamp. Comparisons of the Talbot images before and after the lock in procedure showed that the lens power remained unchanged. The sharp contrast of the interference fringes indicated that the optical quality of the inventive lens also remained unaffected.

To determine if the lock-procedure was complete, the IOL was refitted with a 1 mm diameter photomask and exposed a second time to 0.75 mW/cm² of the 325 laser line for two minutes. As before, no observable change in fringe space or in optical quality of the lens was observed.

EXAMPLE 13

Monitoring for Potential IOL Changes from the Lock-In

A situation may arise wherein the implanted IOL does not require post-operative power modification in such cases, the IOL must be locked in so that its characteristic will not be subject to change. To determine if the lock-in procedure induces undesired changes in the refractive power of a previously unirradiated IOL, the inventive IOL (containing 60 wt % PDMS, 30 wt % RMC monomer E, 10 wt % RMC monomer F, and 0.75 wt % DMPA relative to the two RMC monomers) was subject to three 2 minute irradiations over its entire area that was separated by a 3 hour interval using 0.75 mW/cm² of the 325 laser line from a He:Cd laser. Ronchigramns and moiré fringe patterns were taken prior to and after each subsequent irradiation. The moiré fringe patterns taken of the inventive IOL in air immediately after removal from the lens mold and after the third 2 minute irradiation indicate a focal length of 10.50 mm±0.39 mm (95.24 D±3.69 D) and 10.12 mm±0.39 mm (93.28 D±3.53 D) respectively. These measurements indicate that photo-locking a previously unexposed lens does not induce unwanted changes in power. In addition, no discerrable change in fringe spacing or quality of the Ronchi fringes was detected indicating that the refractive power had not changed due to the lock-in.

EXAMPLE 14

Figure 1B:
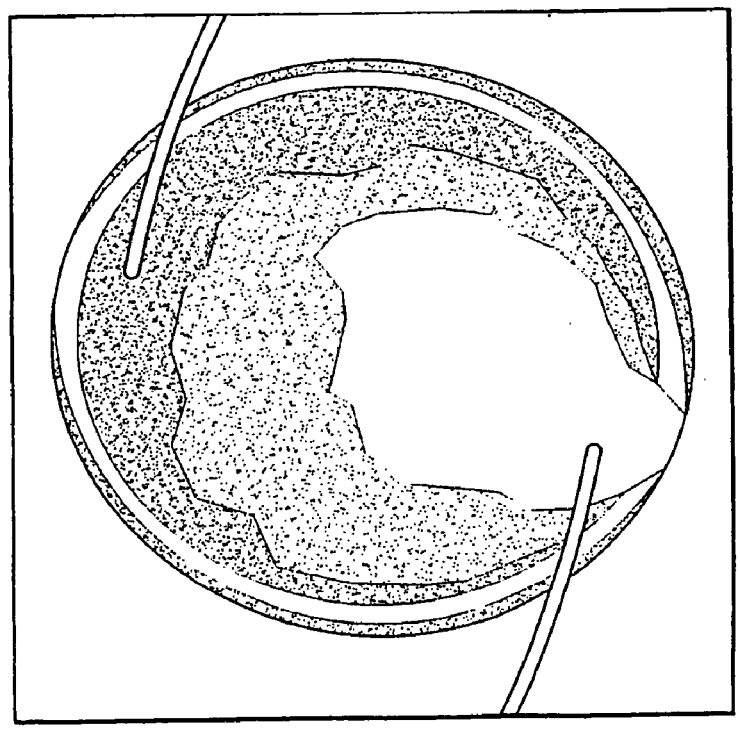

A 6 mm diameter intraocular lens containing a silicone-based MC was prepared using standard molding techniques known to those skilled in the art. The lens had a first polymer matrix prepared from a silicone hydride crosslinked vinyl endcapped diphenylsiloxane dimethylsiloxane. The first polymer matrix comprised about 70 weight % of the lens. The lens also comprised about 30 weight % of a MC (methacrylate endcapped polydimethylsiloxane), 1 weight % (based on MC) of a photoinitiator (benzoin-tetrasiloxane-benzoin), and 0.04 weight % (based on MC) UV absorber. The lens had an initial nominal power of 30 diopters. The center of the lens was then irradiated with 365 nm light using an intensity pattern represented by the equation:

$$I = I_{oe} - \frac{(r - r_c)^2}{2\sigma^2} \quad (1)$$

and an average intensity of 4.12 mW/cm² for 60 seconds. Three hours post-exposure, the lens had a +3.25 D change over the central 2.5 mm region of the lens, which is shown in FIG. 1A. The interference fringes were taken at the preirradiation best focus position. The affected zone is easily observed in the central portion of the light adjustable lens (LAL) and is distinguished by the approximately 6 fringes (in double pass) of defocus in the central portion of the IOL. FIG. 1B depicts a micrograph of FIG. 1A.

In another embodiment, the first polymer matrix comprised about 75 weight % of the lens. The lens also comprised about 25 weight % of a MC (methacrylate endcapped methylphenylsiloxane dimethylsiloxane), 0.83 weight % (based on MC) of a photoinitiator (benzoin-L4-benzoin), and 0.04 weight % (based on MC) UV absorber. The lens had an initial nominal power of +20.0 diopters. The lens was then irradiated with 365 nm (±5 nm) light using a spatial intensity profile described by the following equation:

$$I = I_0 \left( 0.65 \frac{r^2}{r_{max}^2} + 0.35 \right) \quad (2)$$

Figure 2A:
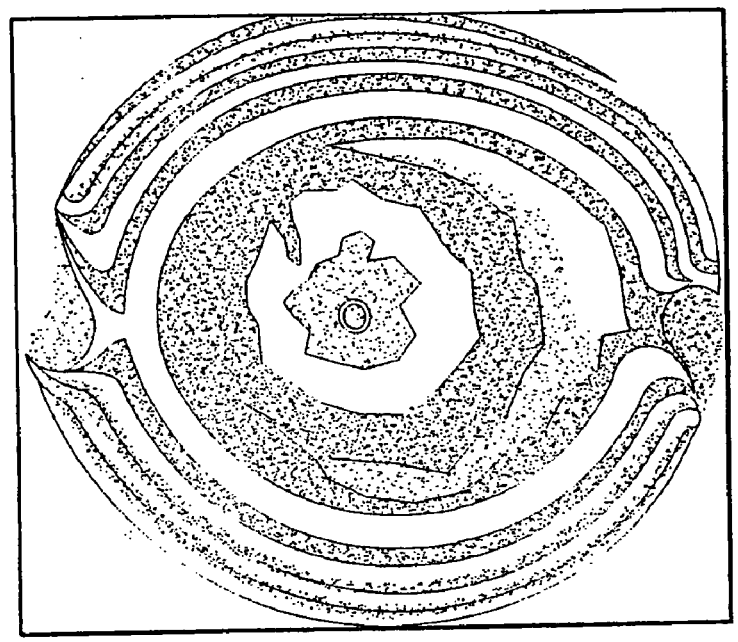
FIGS. 2A and 2B depict a cross-section of a multifocal intraocular lens and a micrograph, according to an embodiment of the invention.
Figure 2B:
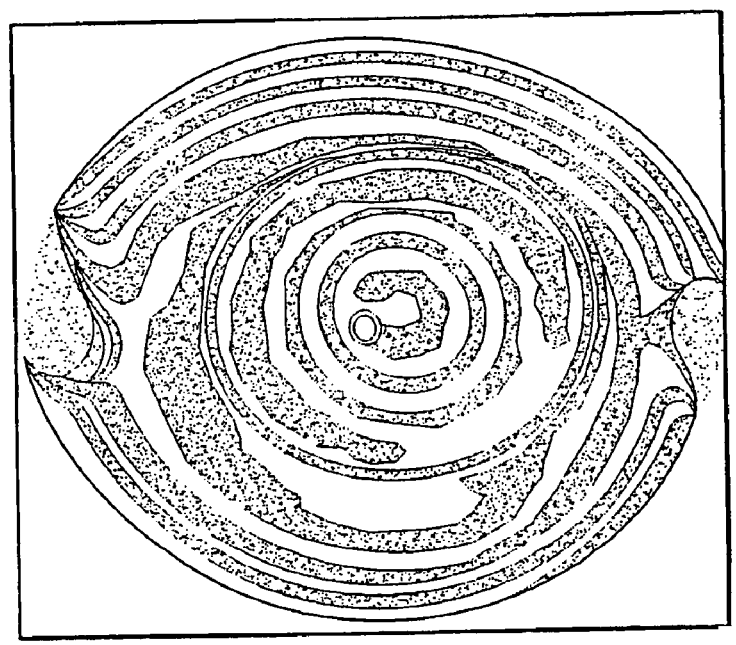

The IOL was irradiated with an average intensity of 6 mW/cm² using three, 15 second exposures separated by 5 seconds. FIGS. 2A and 2B display the interference fringes (in double pass) of the lens before irradiation and 24 hours post irradiation. FIG. 2A depicts the Fizeau interference fringe (in double pass) of a +20.0 D LAL at best focus preirradiation, the same LAL 24 hours after irradiation at the original best focus position. FIG. 2B depicts the LAL of FIG. 2A. The most striking feature between the two interferograms is the presence of a 3 mm reaction zone in the central portion of the lens, which is from the introduction of defocus. The change corresponds to a −0.70 diopters change in this central region.

These two examples illustrate that we can both add and subtract power from the central portion of the lens as well as control the effected zone size.

These two multifocal designs are similar to the bull's eye design described above. The difference between our design and those already presented in the literature and other patents is that we have the ability to affect the change post-operatively after wound healing has occurred, customize the zone size to fit the patient's dilation conditions, add or subtract different amounts of power depending upon the recommendation of the patient or physician, and center the zone along the patient's visual axis once post-operative healing has finished.

EXAMPLE 15

One of the unique aspects of the above described technology is that we have the ability to first change the power of the IOL over the majority of its aperture and then reirradiate the lens over a small zone (0 to 3 mm) to create a bifocal lens as described in example 1. This embodiment has the advantages of first implanting the light adjustable lens in the patient, waiting the required healing time to let the eye refractively stabilize (typically two to four weeks), measuring the refraction of the patient to determine the necessary correction, if any, to bring the patient to emmetropia, irradiating the lens to change the power of the lens over the majority of the aperture, and then reirradiating a smaller zone in the lens (1.5-3 mm) along the patient's visual axis to provide the necessary multifocality for near and distance viewing.

As an example of this, a +20.0 D LAL was molded comprising 75 wt % of silicone matrix, 25 wt % of MC, 0.83 wt % PI, and 0.04 wt % UV absorber. The lens was initially irradiated using an average intensity of 10 mW/cm² using a spatial profile described by equation 2 above. The lens was dosed using seven 15 second exposures (5 seconds between each exposure). This treatment induced −1.32 diopters of change in the lens over a 5.5 region of the aperture. Twenty four hours post-irradiation, the lens was reirradiated in the central portion of the lens using the intensity profile represented by equation 1. The beam size was reduced to 3 mm in diameter, the average intensity of light was 6 mW/cm² and the dose was given in three 30 second doses. Twenty-four hours post irradiation; we observed a change of 1.94 diopters in this central region.

Figure 3A:
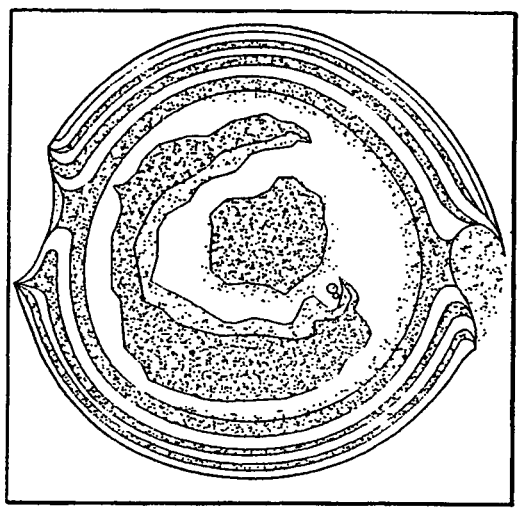
FIGS. 3A through 3C depict interference fringes for a lens, according to an embodiment of the invention.
Figure 3B:
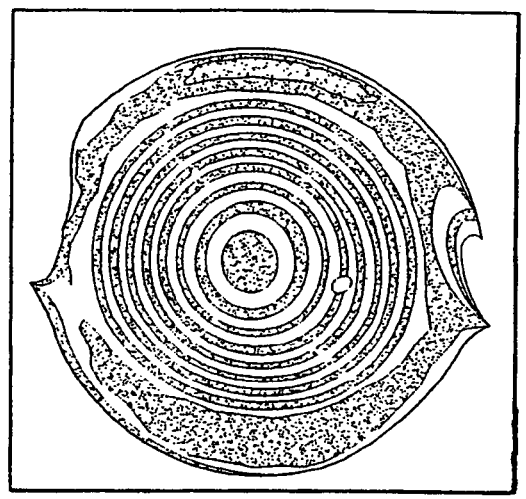
Figure 3C:
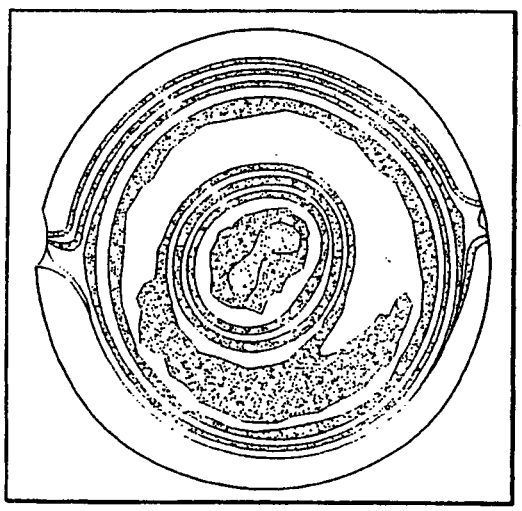

FIG. 3A depicts Fizeau interference fringes (in double pass) of a +20.0 D LAL at best focus preirradiation. FIG. 3B depicts the approximately 8 fringes (in double pass) of defocus introduced by the initial irradiation. This procedure introduced −1.32 diopters of change from the initial base power of +20.0 diopters. FIG. 3C depicts the same LAL at the best focus position 24 hours after the initial irradiation. Note the presence of a new focus zone in the central part of the lens. This zone corresponds to +1.94 diopters of change.

EXAMPLE 16

In the past, the clinical use of bifocal or multifocal IOLs have met with some resistance by patients due to the loss of contrast sensitivity and glare that are inherent to this type of lens' designs. In the past, the only way for a physician to reverse the undesired affects of a previously implanted multifocal or bifocal IOL was to explant the IOL and reinsert it with a standard monofocal IOL. However, the light adjustable lens technology described in this disclosure and previous Calhoun Vision published works provides a means to reverse the multifocal properties of the LAL, effectively returning it to its monofocal condition. Such ability would have the oblivious advantage of reversal without surgical explantation.

Figure 4A:
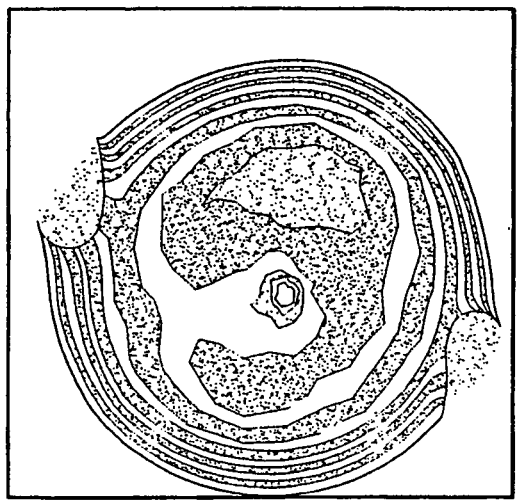
FIGS. 4A through 4C depict an example of reversible multifocality for a lens, according to an embodiment of the invention.

As an example of this process, a +20.0 D LAL was molded comprising 75 wt % of silicone matrix, 25 wt % of MC, 0.83 wt % PI, and 0.04 wt % UV absorber. The preirradiation Fizeau interference fringes are shown in FIG. 4A. This LAL was then irradiated using two successive, 30-second exposures of 6 mW/cm². The spatial intensity profile of this initial irradiation is described by equation 2. As displayed in FIG. 4B, −0.5 D of power were removed from the central optical zone of this lens. Twenty-four hours after this initial irradiation, the LAL was irradiated again using two successive, 30-second exposures of 3 mW/cm². The second irradiation effectively overlaid on top of the initial dose. The spatial intensity profile of this second irradiation is described by equation 1. This second irradiation added +0.5 D of power to the initially irradiated region, effectively removing the initial subtraction of power from the LAL and showing an example of multifocal reversibility in the Calhoun Vision LAL.

Figure 4B:
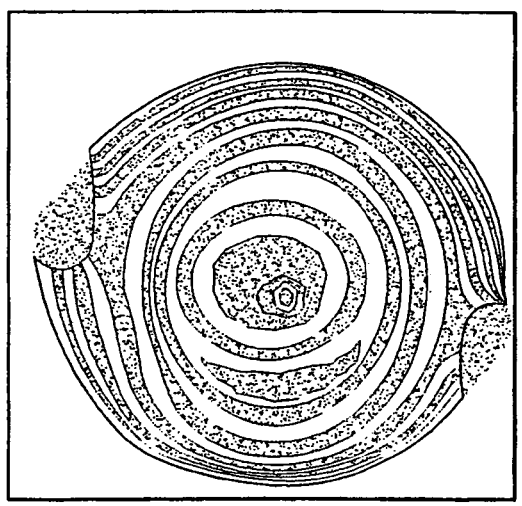
Figure 4C:
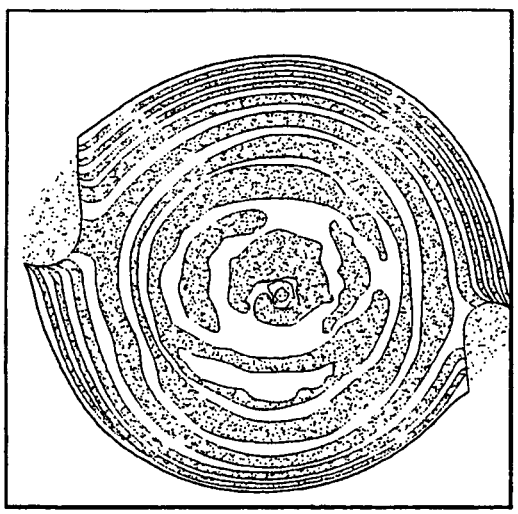

FIGS. 4A, 4B and 4C depict an example of reversible multifocality. FIG. 4A depicts preirradiation Fizeau interference fringes of a +20.0 diopters LAL at best focus. FIG. 4B Fizeau interference fringes at the preirradiation best focus 24 hours post initial irradiation. Note that −0.5 diopters of spherical power have been subtracted from the central portion of the LAL as noted by the fringes of defocus in the central portion of the LAL. FIG. 4C depicts Fizeau interference fringes at the preirradiation best focus position two hours post the second irradiation showing the removal of the defocus fringes. This indicates that the LAL has been effectively brought back to its preirradiation power.

FIG. 5 depicts an example of a lens 500 formed according to embodiments of the invention. The lens includes a plurality of different focal zones, 501, 502, 503, 504, 505, and 506. Note that the number of zones is by way of example only, as more or fewer zones could be used. For example, there may be five concentric annular zones. The different zones are preferably concentric about a central zone 501. The different zones may have different radial widths, e.g. zone 504 has a smaller radial width than zone 503. Similarly, the different zones may have different areas, e.g. the area of zone 501 is smaller than the area of zone 503. Alternatively, some or all of the zones may have the same radial width and/or area as other zones. Each zone may have a different focal length or diopter than each of the other zones, e.g. zone 502 may be +1.0 diopter with respect to zone 501, and zone 503 may be +1.0 diopter with respect to zone 502, etc. Alternatively, some zones may have the same power, while other zones have different powers. For example, zones 501, 503, and 505 may have the same power, while zones 502, 504, and 506 may be +1.0 diopter with respect to zone 501. As another example, zones 501, 503, and 505 may have the same power, while zone 502 may be +1.0 diopter with respect to zone 501, zone 504 may be +1.0 diopter with respect to zone 502, and zone 506 may be +1.0 diopter with respect to zone 504. Note that some zones may have a negative diopter with respect to other zones. Further note that the different zones may correct for near vision, while other zones correct for far vision. The different zones may be in a pattern other than a "bulls-eye" patterns, e.g. a cylindrical pattern, which would be used to correct astigmatism. Any pattern zones may be formed into the lens. Lens 501 may be a eyeglass lens, a lens used in an optical system, or an intra-ocular lens. Note that a lens is used by way of example only, as other optical elements could be used. Further note that each zone may be spherical or aspherical.

FIGS. 6A and 6B depict a top-down view and a side view of an example of a multifocal lens 60 according to embodiments of the invention. Lens 60 includes region 61 that provides a user with near vision and region 62 provides a user with far vision.

FIGS. 6C-6F depict an example of a method of forming the lens of FIGS. 6A and 6B. The lens 60 comprises a photosensitive macromer 63 in a matrix 64. In FIG. 6A, the central zone of the lens 60 is selectively irradiated by radiation 65, e.g. ultraviolet light or near ultraviolet light (365 nanometers). The radiation causes the macromers 63 to from an interpenetrating network within the target area (the central zone), in other words the macromers 63 form polymerized macromers 66, in FIG. 6D. The formation of the polymerized macromers 66 produces a change in the chemical potential between the irradiated and unirradiated regions of the lens. To reestablish thermodynamic equilibrium, macromers 63 from the unirradiation portion 62 of the lens will diffuse into the irradiated portion, which produces a swelling in the irradiation portion 61, as shown in FIG. 6E. The swelling, in turn, changes the curvature of the lens.

By controlling the irradiation dosage (e.g. beam location, beam intensity), spatial intensity profile, and the target area, physical changes in the radius of curvature of the lens surface are achieved, thus modifying the refractive power of the lens. The characteristics of the lens may be modified to change the power of the lens, the spherical nature of the lens, the aspherical nature of the lens, reduce or eliminate astigmatic error, or correct other higher order aberrations. The application of the radiation 65 may be repeated until a desired amount of change has occurred. The radiation doses may be varied, e.g. one application corrects for astigmatism, while another application may provide the central add.

Alternatively, the radiation may be controlled such that a single dose induces all desired effects.

After the lens has the desired optical characteristics, the lens is locked-in, as shown in FIG. 6E. During lock-in, the surface of the lens is irradiated by radiation 67 to polymerize most of the remaining unreacted macromer 63. This prevents any subsequent substantial change in lens characteristics from macromer diffusion. The completed lens is shown in FIG. 6F with the permanent change power and/or other characteristic(s).

Note that the it is desirable to irradiate the entire surface of the lens during lock-in, however, there may be some portions of the lens surface that cannot be irradiated because of its placement an optical system. For example, an interocular lens has been implanted into the eye of an animal (e.g. a human, rabbit, etc.), some portion(s) of the lens may be blocked by a feature(s) of the animal.

Note that prior to lock-in, if the change has become undesirable to the patient, the process may be reversed, so as to remove the change. The reversal would be done by irradiating the lens with a complementary pattern to that which was used to provide the change. This would cause diffusion of the macromer to peripheral portion of the lens and would compensate for the initial change, e.g. central add 61.

FIGS. 6A-6F depict a lens that has a central add, e.g. wherein the central zone has more diopters in power as compared with the surrounding area. A similar process can be used to produce a central subtract, e.g. by irradiating the outer periphery (not the central zone), which would cause a swelling of the outer periphery (and thus a dip or concave curvature in the central zone) and result in a decrease in the lens power of the lens.

In conditions of bright ambient light, e.g. driving a car into the sun, the pupil of the-eye may close such that the far zone 62 of lens 60 is entirely blocked, leaving the user with only near vision. In such a case a lens such as lens 70 of FIGS. 7A and 7B may be preferable. FIGS. 7A and 7B depict a top-down view and a side view of an example of a multifocal lens 70 according to embodiments of the invention. Lens 70 includes regions 71 and 73 that provides a user with far vision, and while annulus region 72 provides a user with near vision.

FIGS. 7C-7F depict an example of a method of forming the lens of FIGS. 7A and 7B. The lens 70 comprises a photosensitive macromer 73 in a matrix 74. In FIG. 7A, an annular zone 72 that surrounds the central zone 71 of the lens 70 is selectively irradiated by radiation 75, e.g. ultraviolet light or near ultraviolet light (365 nanometers). The radiation causes the macromers 73 to from an interpenetrating network within the target area (the annular zone), in other words the macromers 73 form polymerized macromers 76, in FIG. 7D. The formation of the polymerized macromers 76 produces a change in the chemical potential between the irradiated and unirradiated regions of the lens. To re-establish thermodynamic equilibrium, macromers 73 from the unirradiation portion 71 of the lens will diffuse into the irradiated portion, which produces a swelling in the irradiation portion 72, as shown in FIG. 7E. The swelling, in turn, changes the curvature of the lens.

By controlling the irradiation dosage (e.g. beam location, beam intensity), spatial intensity profile, and the target area, physical changes in the radius of curvature of the lens surface are achieved, thus modifying the refractive power of the lens. The characteristics of the lens may be modified to change the power of the lens, the spherical nature of the lens, the aspherical nature of the lens, reduce or eliminate astigmatic error, or correct other higher order aberrations. The application of the radiation 75 may be repeated until a desired amount of change has occurred. The radiation doses may be varied, e.g. one application corrects for astigmatism, while another application may provide the annular add. Alternatively, the radiation may be controlled such that a single dose induces all desired effects.

After the lens has the desired optical characteristics, the lens is locked-in, as shown in FIG. 7E. During lock-in, the surface of the lens is irradiated by radiation 77 to polymerize most of the remaining unreacted macromer 73. This prevents any subsequent substantial change in lens characteristics from macromer diffusion. The completed lens is shown in FIG. 7F with the permanent change power and/or other characteristic(s).

Note that the it is desirable to irradiate the entire surface of the lens during lock-in, however, there may be some portions of the lens surface that cannot be irradiated because of its placement an optical system. For example, an interocular lens has been implanted into the eye of an animal (e.g. a human, rabbit, etc.), some portion(s) of the lens may be blocked by a feature(s) of the animal.

Note that prior to lock-in, if the change has become undesirable to the patient, the process may be reversed, so as to remove the change. The reversal would be done by irradiating the lens with a complementary pattern to that which was used to provide the change. This would cause diffusion of the macromer to peripheral portion of the lens and would compensate for the initial change, e.g. annular add 72.

FIGS. 7A-7F depict a lens that has an annular add, e.g. wherein the annular zone has more diopters in power as compared with the surrounding area and the central zone. A similar process can be used to produce an annular subtract, e.g. by irradiating the outer periphery and the central zone (not the annular zone), which would cause a swelling of the outer periphery and the central zone (and thus a dip or concave curvature in the annular zone) and result in a decrease in the lens power of the lens.

As discussed above, after implantation of an IOL, the lens may shift due to the healing of the patient. The shift may be a lateral shift in a direction that is orthogonal to the optical axis. In such a case, the base power may be adjusted and/or the multifocal power may be added after healing to compensate for the shift. FIG. 8 depict a top-down view an example of a multifocal lens 80 according to embodiments of the invention. Lens 80 includes region 81 having a first power and region 82 having a second power. Region 81 is located off center of the lens 80 to correlate with the center of the optical axis of the patient in which lens 80 is implanted. Similarly, region 82 may also be shifted to correspond to the optical axis of the patient.

Figure 9:
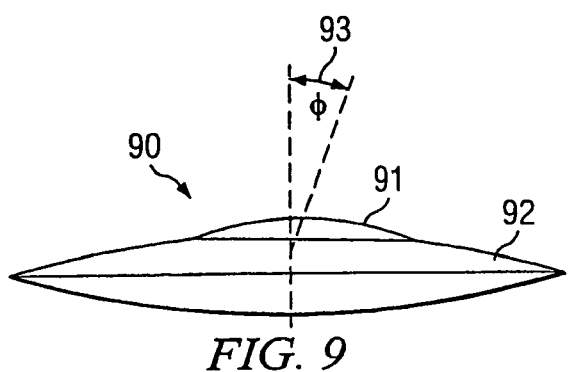
FIG. 9 depicts a side view of an example of a multifocal lens according to embodiments of the invention.

The shift may also be an angular shift, in other words, the lens may be centered correctly, but may be tilted with respect to the optical axis of the patient. In such a case, the base power may be shifted and/or the multifocal power may be added after healing to compensate for the shift. FIG. 9 depict a side view an example of a multifocal lens 90 according to embodiments of the invention. Lens 90 includes region 91 having a first power and region 92 having a second power. Region 91 is tilted at angle $\phi$ 93 with respect to an optical axis of the lens (before adding the region 91 and/or adjusting region 92) to correspond to the optical axis of the patient in which the lens 90 is implant. The shift may also encompass both a lateral shift and/or a tilt. In which case a lens that includes aspects of FIGS. 8 and 9 would be preferable. Furthermore, a lens may include aspects of FIGS. 8 and/or 9, as well as FIG. 6A or FIG. 7A Note that the size and power of the multifocal zones may be selected based on the pupil dilation of the patient in which the lens is implanted. In other words, placement and size of the near and distance vision portions may be selected based on the pupil dilation response. Thus, for a particular patient, the sizes and placement may be selected to allow for one or both of near and distance vision when the pupil is maximally dilated. The size and power may also be selected based on the habits of the patient. For example a person that holds reading material close to their face (or eyes) for reading may prefer a size and/or power that is different from a person that holds reading material farther from their face (or eyes). As another example, a person that does most of their reading from a computer screen may like to have a reading distance of 24 inches, while a person that mostly reads books or newspapers may like to have a reading distance of 12-18 inches.

Figure 10B:
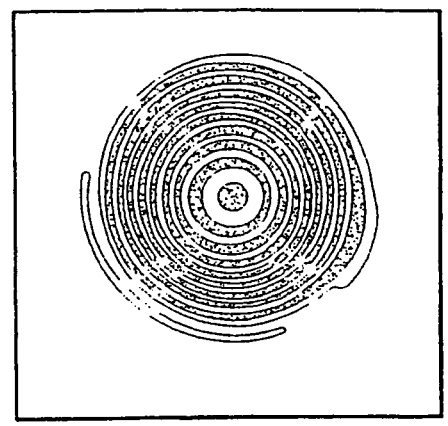
FIGS. 10A-10D depict a series of interference patterns of a lens according to embodiments of the invention.
Figure 10A:
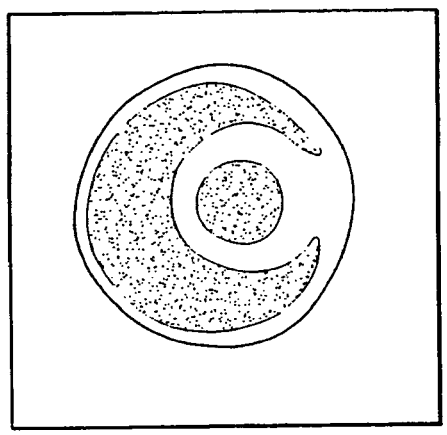
Figure 10D:
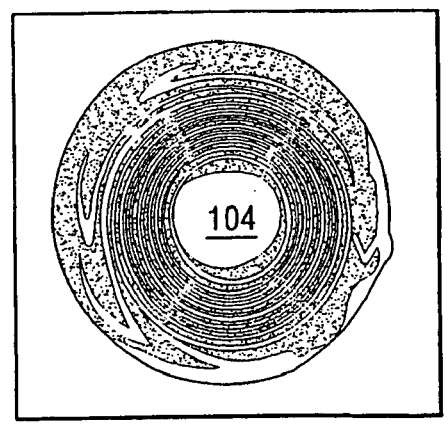
Figure 10C:
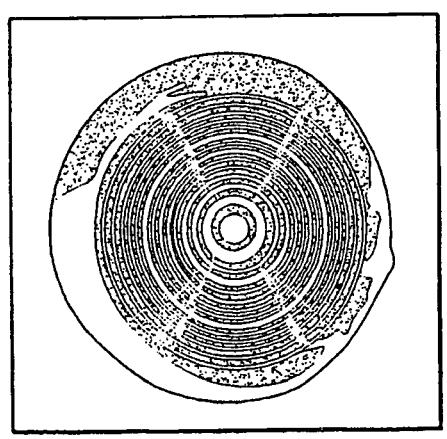

The following is an example of a clinical scenario to illustrate creating a multifocal LAL according to embodiments of the invention. A cataract patient has a LAL implanted and after postoperative healing, manifest refraction indicates that the patient requires a −2.0 D change in the LAL power to obtain emmetropia. FIG. 10A illustrates the interference pattern 100 of the unirradiated LAL at its preirradiation best focus position along the optical axis of the interferometer. A common practice among cataract surgeons is to leave the patient slightly myopic in at least one eye so that only −1.4 D of power is initially removed from the LAL, which is shown the interference pattern 101 in FIG. 10B. The patient is then allowed a time period, e.g. few hours or days, to see how well this correction is tolerated. For purposes of this example, assume that the patient now desires to be brought to emmetropia. An additional dose of radiation will adjust the base power of the lens. FIG. 10C shows the interference pattern 102 of the LAL at the original preirradiation best focus position 24 hours after the second spherical irradiation correction. A comparison of FIGS. 10B and 10C shows an increase in the number of fringes of defocus, i.e. OPD, which corresponds to an additional −0.6 D of correction or −2.0 D of overall power change. After bringing the patient to emmetropia, the ophthalmologist can impart multifocality to the LAL by irradiating a third time. In this example, a 2 mm zone in the central part of the LAL (the Bull's Eye configuration) was irradiated to add back +2.0 D of power to the LAL. This is shown in FIG. 10D, which shows that a central part 104 of the LAL has been brought back to its initial refractive power. When finished adjusting the lens, the LAL may be irradiated for lock-in, which prevents ambient radiation from changing the LAL. Lock-in radiation consumes most of the remaining light reactive material in the LAL.

Note that in the above examples, the multifocal zone or zones has been spherical (e.g. 61 of FIG. 6B) or circular (e.g. 61 of FIG. 6A) in nature. However, noncircular and/or nonspherical zones may be used. For example, a multifocal zone may be aspherically shaped along an axis through the lens (e.g. vertically in the view of FIG. 6B). A lens may be elliptically shaped, cylindrically shaped, or rectangularly shaped along an axis across the lens (e.g. horizontally in the view of FIG. 6A).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A multifocal lens comprising:
   a first portion of the lens has a first focal length that provides distance vision; and
   a second portion of the lens that includes a material that is optically reactive to an external stimulus and has a focal length that is adjusted to a second focal length by application of the stimulus and provides near vision;
   wherein the second portion has a substantially circular shape and is located at a center of the lens, and the first portion has a substantially annulus shape and is located around the second portion.

2. A multifocal lens comprising:
   a first portion of the lens has a first focal length that provides distance vision;
   a second portion of the lens that includes a material that is optically reactive to an external stimulus and has a focal length that is adjusted to a second focal length by application of the stimulus and provides distance vision; and
   a third portion of the lens that has the first focal length;
   wherein the first portion has a substantially circular shape and is located at a center of the lens, and the second portion has a substantially annulus shape and is located around the first portion, and the third portion has a substantially annulus shape and is located around the second portion.

3. A multifocal lens comprising:
   a first portion of the lens has a first focal length; and
   a second portion of the lens that includes a material that is optically reactive to an external stimulus and has a focal length that is adjusted to a second focal length by application of the stimulus;

wherein the first focal length is different from the second focal length, and the second portion has a substantially circular shape and is located at non-central portion of the lens, and the first portion is located around the second portion.

4. A multifocal lens comprising:

a first portion of the lens has a first focal length that is located on a first side of the lens; and a second portion of the lens that includes a material that is optically reactive to an external stimulus and has a focal length that is adjusted to a second focal length by application of the stimulus;

wherein the first focal length is different from the second focal length, and the second portion has an optical axis that is at an angle with respect to an optical axis of the second side of the lens.

5. A method for using a lens comprising:

preparing a lens having a modifying composition (MC) dispersed therein, wherein the modifying composition is capable of stimulus-induced polymerization;

implanting the lens in an animal;

exposing a portion of the lens to an external stimulus that causes changes in the optical properties that change a focal length of the portion of the lens to a first focal length to reduce an error caused by a healing response of the animal;

exposing another portion of the lens to an external stimulus that causes changes in the optical properties that change a focal length of the portion of the lens to a second focal length that is different from the first focal length.

6. The method of claim 5, further comprising:

selecting at least one of the first focal length and the second focal length based on a habit of the animal.

7. The method of claim 5, further comprising:

selecting a size of at least one of the portion and the another portion based on a habit of the animal.

8. The method of claim 5, further comprising:

selecting a size of at least one of the portion and the another portion based on a pupil dilation response of the animal.

* * * * *